(12) United States Patent
Lubisch et al.

(10) Patent No.: US 7,276,500 B2
(45) Date of Patent: Oct. 2, 2007

(54) SUBSTITUTED AMIDES, THEIR PREPARATION AND USE

(75) Inventors: Wilfried Lubisch, Heidelberg (DE); Achim Möller, Grünstadt (DE); Hans-Jörg Treiber, Brühl (DE); Monika Knopp, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 644 days.

(21) Appl. No.: 10/690,400

(22) Filed: Oct. 20, 2003

(65) Prior Publication Data
US 2004/0082569 A1 Apr. 29, 2004

Related U.S. Application Data

(62) Division of application No. 09/673,089, filed as application No. PCT/EP99/02633 on Apr. 20, 1999, now Pat. No. 6,753,327.

(30) Foreign Application Priority Data
Apr. 20, 1998 (DE) .................... 198 18 615

(51) Int. Cl.
| | | |
|---|---|---|
| A61K 31/5377 | (2006.01) | |
| A61K 31/496 | (2006.01) | |
| A61K 31/4439 | (2006.01) | |
| A61K 31/444 | (2006.01) | |
| A61K 31/44 | (2006.01) | |
| C07D 213/82 | (2006.01) | |

(52) U.S. Cl. .............. 514/235.5; 514/253.13; 514/318; 514/343; 514/355; 544/131; 544/365; 546/146; 546/194; 546/276.4; 546/277.1; 546/316

(58) Field of Classification Search .......... None
See application file for complete search history.

(56) References Cited

FOREIGN PATENT DOCUMENTS

| DE | 196 42 591 A1 | 4/1998 |
|---|---|---|
| EP | 0 520 336 A2 | 12/1993 |
| WO | WO92/12140 | 7/1992 |
| WO | WO92/18850 | 7/1992 |
| WO | WO94/00095 | 6/1993 |
| WO | WO95/00535 | 1/1995 |
| WO | WO99/54310 | 10/1999 |

OTHER PUBLICATIONS

S. Mehdi, Cell-penetrating Inhibitors of Calpain, Trends in Bio. Sci. 1991, 16, 150-153.
Angelastro et al., Journal of Medicinal Chemistry, 1990, 11-13.
Harbeson et al., Stereospecific Synthesis of Peptidyl a-Keto Amides as Inhibitors of Calpain, Journal of Medicinal Chemistry, 1994, 2918-2929.
Burkhardt, Oxidation of a-Hydroxy Esters to a-Keto Esters Using the Dess-Martin Periodinane Reagent, Tet. Letters vol. 29, No. 28, p. 3433-3436 (1988).

Primary Examiner—Emily Bernhardt
(74) Attorney, Agent, or Firm—Wood Phillips et al.

(57) ABSTRACT

An amide of the formula I and its tautomeric forms, possible enantiomeric and diastereomeric forms, E and Z forms, and possible physiologically tolerated salts, in which the variables have the following meanings:

A —$(CH_2)_p$—$R^1$, where $R^1$ can be pyrrolidine [sic], morpholine [sic], piperidine [sic], —$NR^5R^6$ and and $R^5$, $R^6$ and $R^7$ can, independently of one another, be hydrogen, $C_1$-$C_4$-alkyl, $CH_2Ph$, $Ph$, $CH_2CH_2Ph$, it also being possible for the phenyl rings to be substituted by $R^6$, and p can be 1 and 2, and
B can be phenyl [sic], pyridyl [sic], pyrimidyl [sic] and pyridazyl [sic], it also being possible for the rings to be substituted by up to 2 $R^8$ radicals, and
D can be a bond, —$(CH_2)_m$—, —CH=CH—, —C≡C—, and
$R^2$ is chlorine, bromine, fluorine, $C_1$-$C_6$-alkyl, NHCO—$C_1$-$C_4$-alkyl, NHSO$_2$—$C_1$-$C_4$-alkyl, NO$_2$, —O—$C_1$-$C_4$-alkyl and NH$_2$, and
$R^3$ is —$C_1$-$C_6$-alkyl, branched or unbranched, and which may also carry a phenyl ring, indolyl ring or cyclohexyl ring which is in turn substituted by by [sic] a maximum of two $R^8$ radicals, where $R^8$ is hydrogen, $C_1$-$C_4$-alkyl, branched or unbranched, —O—$C_1$-$C_4$-alkyl, OH, Cl, F, Br, I, CF$_3$, NO$_2$, NH$_2$, CN, COOH, COO—$C_1$-$C_4$-alkyl, NHCO—$C_1$-$C_4$-alkyl, —NHSO$_2$-$C_1$-$C_4$-alkyl and —SO$_2$—$C_1$-$C_4$-alkyl; and
Y is phenyl [sic], pyridine, pyrimidine and pyrazine and
$R^4$ is hydrogen, COOR$^9$ and CO-Z in which Z is NR$^{10}$R$^{11}$ and $R^9$ is hydrogen, $C_1$-$C_6$-alkyl, linear or branched, and which may [lacuna] substituted by a phenyl ring which may itself also be substituted by one or two $R^{12}$ radicals, and $R^{10}$ is hydrogen, $C_1$-$C_6$-alkyl, linear or branched, and which may [lacuna] substituted by a phenyl ring which itself may also be substituted by one or two $R^{12}$ radicals, and

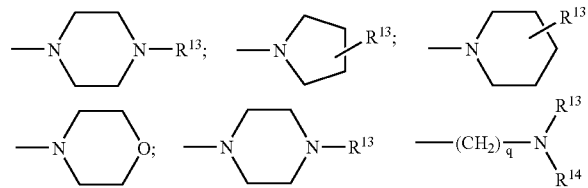

$R^{11}$ is hydrogen, $C_1$-$C_6$-alkyl, branched or unbranched, which may also be and [sic] substituted by a phenyl ring which may also carry an $R^9$ radical, and $R^{12}$ can be hydrogen, $C_1$-$C_4$-alkyl, branched or unbranched, —O—$C_1$-$C_4$-alkyl, OH, Cl, F, Br, J, $CF_3$, $NO_2$, $NH_2$, CN, COOH, COO—$C_1$-$C_4$-alkyl, —NHCO—$C_1$-$C_4$-alkyl, —NHCO-phenyl, —$NHSO_2$—$C_1$-$C_4$-alkyl, $NHSO_2$-phenyl, —$SO_2$—$C_1$-$C_4$-alkyl and —$SO_2$-phenyl, $R^{13}$ is hydrogen, $C_1$-$C_6$-alkyl, linear or branched, and which may [lacuna] substituted by a phenyl ring which may itself also be substituted by one or two $R^{12}$ radicals, and $R^{14}$ is hydrogen, $C_1$-$C_6$-alkyl, linear or branched, and which may [lacuna] substituted by a phenyl ring which may itself also be substituted by one or two $R^{12}$ radicals, and n is a number 0, 1 or 2, and m, q are, independently of one another, a number 0, 1, 2, 3 or 4.

4 Claims, No Drawings

SUBSTITUTED AMIDES, THEIR PREPARATION AND USE

This application is a division of U.S. application Ser. No. 09/673,089, flied Oct. 11, 2000, now U.S. Pat. No. 6,753,327 which is a national phase application of PCT/EP 99/02633 filed Apr. 20, 1999 which claims the priority of German patent application No. 19818615.0 filed Apr. 20, 1998.

The present invention relates to novel amides which are inhibitors of enzymes, especially cysteine proteases such as calpain (=calcium dependant cysteine proteases) and its isoenzymes and cathepsins, for example B and L.

Calpains are intracellular proteolytic enzymes from the group of cysteine proteases and are found in many cells. Calpains are activated by an increase in the calcium concentration, a distinction being made between calpain I or µ-calpain, which is activated by µ-molar concentrations of calcium ions, and calpain II or m-calpain, which is activated by m-molar concentrations of calcium ions (P. Johnson, Int. J. Biochem. 1990, 22(8), 811-22). Further calpain isoenzymes have now been postulated too (K. Suzuki et al., Biol. Chem. Hoppe-Seyler, 1995, 376(9), 523-9).

It is suspected that calpains play an important part in various physiological processes. These include cleavages of regulatory proteins such as protein kinase C, cytoskeletal proteins such as MAP 2 and spectrin, muscle proteins, protein degradation in rheumatoid arthritis, proteins in the activation of platelets, neuropeptide metabolism, proteins in mitosis and others which are listed in M. J. Barrett et al., Life Sci. 1991, 48, 1659-69 and K. K. Wang et al., Trends in Pharmacol. Sci., 1994, 15, 412-9.

Elevated calpain levels have been measured in various pathophysiological processes, for example: ischemias of the heart (e.g. myocardial infarct), of the kidney or of the central nervous system (e.g. stroke), inflammations, muscular dystrophies, cataracts of the eyes, injuries to the central nervous system (e.g. trauma), Alzheimer's disease etc. (see K. K. Wang, above). It is suspected that there is a connection between these disorders and elevated and persistent intracellular calcium levels. This results in overactivation of calcium-dependent processes, which are then no longer subject to physiological control. Accordingly, overactivation of calpains may also induce pathophysiological processes.

It has therefore been postulated that inhibitors of calpain enzymes may be useful for treating these disorders. Various investigations have confirmed this. Thus, Seung-Chyul Hong et al., Stroke 1994, 25(3), 663-9 and R. T. Bartus et al., Neurological Res. 1995, 17, 249-58 have shown a neuroprotective effect of calpain inhibitors in acute neurodegenerative disorders or ischemias like those occurring after stroke. Likewise, calpain inhibitors improved the recovery of the memory deficits and neuromotor disturbances occurring after experimental brain trauma (K. E. Saatman et al. Proc. Natl. Acad. Sci. USA, 1996, 93, 3428-3433). C. L. Edelstein et al., Proc. Natl. Acad. Sci. USA, 1995, 92, 7662-6, found a protective effect of calpain inhibitors on kidneys damaged by hypoxia. Yoshida, Ken Ischi et al., Jap. Circ. J. 1995, 59(1), 40-8, were able to show beneficial effects of calpain inhibitors after cardiac damage produced by ischemia or reperfusion. Since the release of the β-AP4 protein is inhibited by calpain inhibitors, a potential therapeutic use for Alzheimer's disease has been proposed (J. Higaki et al., Neuron, 1995, 14, 651-59). The release of interleukin-1α is likewise inhibited by calpain inhibitors (N. Watanabe et al., Cytokine 1994, 6(6), 597-601). It has further been found that calpain inhibitors have cytotoxic effects on tumor cells (E. Shiba et al. 20th Meeting Int. Ass. Breast Cancer Res., Sendai Jp, 1994, 25-28 Sept., Int. J. Oncol. 5 (Suppl.), 1994, 381). Further possible uses of calpain inhibitors are detailed in K. K. Wang, Trends in Pharmacol. Sci., 1994, 15, 412-8.

Calpain inhibitors have already been described in the literature. However, these are predominantly either irreversible or peptide inhibitors. Irreversible inhibitors are usually alkylating substances and have the disadvantage that they react nonselectively or are unstable in the body. Thus, these inhibitors often show unwanted side effects such as toxicity, and are accordingly of limited use or unusable. The irreversible inhibitors can be said to include, for example, the epoxides E 64 (E. B. McGowan et al., Biochem. Biophys. Res. Commun. 1989, 158, 432-5), α-halo ketones (H. Angliker et al., J. Med. Chem. 1992, 35, 216-20) or disulfides (R. Matsueda et al., Chem. Lett. 1990, 191-194).

Many known reversible inhibitors of cysteine proteases such as calpain are peptide aldehydes, in particular dipeptide and tripeptide aldehydes such as, for example, Z-Val-Phe-H (MDL 28170) (S. Mehdi, Trends in Biol. Sci. 1991, 16, 150-3). Under physiological conditions, peptide aldehydes have the disadvantage that, owing to the high reactivity, they are often unstable, may be rapidly metabolized and are prone to nonspecific reactions which may cause toxic effects (J. A. Fehrentz and B. Castro, Synthesis 1983, 676-78).

JP 08183771 (CA 1996, 605307) and EP 520336 have described aldehydes-derived from 4-piperidinoylamides [sic] and 1-carbonyl-4-piperidinoylamides [sic] as calpain inhibitors. However, the aldehydes which are claimed herein and are derived from amides of the general structure I with heteroaromatic substituents have previously been described [sic]

Peptide ketone derivatives are likewise inhibitors of cysteine proteases, in particular calpains. Thus, for example, ketone derivatives where the keto group is activated by an electron-attracting group such as $CF_3$ are known to be inhibitors of serine proteases. In the case of cysteine proteases, derivatives with ketones activated by $CF_3$ or similar groups have little or no activity (M. R. Angelastro et al., J. Med. Chem. 1990, 33, 11-13). Surprisingly, to date only ketone derivatives in which, on the one hand, leaving groups in the α position cause irreversible inhibition and, on the other hand, the keto group is activated by a carboxylic acid derivative have been found to be effective inhibitors of calpain (see M. R. Angelastro et al., see above; WO 92/11850; WO 92,12140; WO 94/00095 and WO 95/00535). However, only peptide derivatives of these keto amides and keto esters have to date been described as effective (Zhaozhao Li et al., J. Med. Chem. 1993, 36, 3472-80; S. L. Harbenson et al., J. Med. Chem. 1994, 37, 2918-29 and see above M. R. Angelastro et al.).

Ketobenzamides have already been described in the literature. Thus, the keto ester PhCO—Abu-COOCH$_2$CH$_3$ has been described in WO 91/09801, WO 94/00095 and 92/11850. The analogous phenyl derivative Ph—CONH—CH(CH$_2$Ph)—CO—COOCH$_3$ was, however, found to be only a weak calpain inhibitor in M. R. Angelastro et al., J. Med. Chem. 1990, 33, 11-13. This derivative is also described in J. P. Burkhardt, Tetrahedron Lett., 1988, 3433-36. The significance of the substituted benzamides has, however, never been investigated to date.

In a number of therapies, such as for stroke, the active ingredients are administered intravenously, for example as infusion solution. To do this it is necessary to have available substances, in this case calpain inhibitors, which have adequate solubility in water so that an infusion solution can be prepared. Many of the described calpain inhibitors have, however, the disadvantage that they have only low or no solubility in water and thus are unsuitable for intravenous administration. Active ingredients of this type can be administered only with ancillary substances intended to confer solubility in water (cf. R. T. Bartus et al. J. Cereb. Blood Flow Metab. 1994, 14, 537-544). These ancillary substances, for example polyethylene glycol, often have side effects, however, or are even incompatible. A non-peptide calpain inhibitor which is soluble in water without ancillary substances would thus be a great advantage. No such inhibitor has been described to date, and it would thus be novel.

Non-peptide aldehydes, keto carboxylic esters and keto amide derivatives were described in the present invention. These compounds are novel and surprisingly show the possibility of obtaining potent non-peptide inhibitors of cysteine proteases, such as, for example, calpain, by incorporating rigid structural fragments. In addition, all the present compounds of the general formula I have at least one aliphatic amine radical and are thus able to bind [sic] salts with acids. This results in improved solubility in water and thus the compounds show the required profile for intravenous administration as is necessary, for example, for stroke therapy.

The present invention relates to amides which have heterocyclic substituents and the general formula I

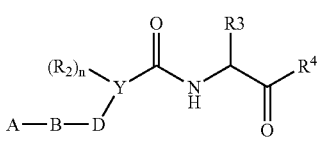

and their tautomeric and isomeric forms, possible enantiomeric and diastereomeric forms, and possible physiologically tolerated salts, in which the variables have the following meanings:

A —$(CH_2)_p$—$R^1$, where $R^1$ can be pyrrolidine [sic], morpholine [sic], hexahydroazepine [sic], piperidine [sic], —$NR^5R^6$ and

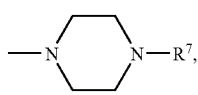

it also being possible for the cyclic amines to be substituted by one or two $R^{15}$ radicals, and $R^{15}$ are [sic] hydrogen, $C_1$-$C_6$-alkyl, O—$C_1$-$C_6$-alkyl and phenyl, and $R^5$, $R^6$ and $R^7$ can be, independently of one another, hydrogen, $C_1$-$C_4$-alkyl, cyclohexyl, cyclopentyl, $CH_2Ph$, Ph, $CH_2CH_2Ph$, it also being possible for the phenyl rings to be substituted by $R^6$, and p can be 1 and 2, and B can be phenyl [sic], pyridyl [sic], pyrazyl [sic], pyrimidyl [sic] and pyridazyl [sic], it also being possible for the rings to be substituted by up to 2 $R^8$ radicals, and A and B together can also be

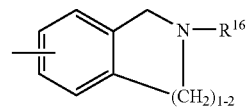

and $R^{16}$ is hydrogen, $C_1$-$C_6$-alkyl and $(CH_2)_{1-4}$-phenyl, it also being possible for the phenyl ring to be substituted by a maximum of 2 $R^6$ radicals, and D can be a bond, —$(CH_2)_{0-2}$—O—$(CH_2)_{0-2}$, —$(CH_2)_m$—, —CH=CH—, —C≡C—, and $R^2$ is chlorine, bromine, fluorine, $C_1$-$C_6$-alkyl, NHCO—$C_1$-$C_4$-alkyl, NHSO$_2$—$C_1$-$C_4$-alkyl, NO$_2$, —O—$C_1$-$C_4$-alkyl and NH$_2$, and $R^3$ is —$C_1$-$C_6$-alkyl, branched or unbranched, and which may also carry a SCH$_3$ radical, a phenyl ring, imidazolyl ring, indolyl ring and cyclopentyl, cycloheptyl or cyclohexyl ring which is in turn substituted by by [sic] a maximum of two $R^8$ radicals, where $R^8$ is hydrogen, $C_1$-$C_4$-alkyl, branched or unbranched, —O—$C_1$-$C_4$-alkyl, OH, Cl, F, Br, I, CF$_3$, NO$_2$, NH$_2$, CN, COOH, COO—$C_1$-$C_4$-alkyl, NHCO—$C_1$-$C_4$-alkyl, —NHSO$_2$—$C_1$-$C_4$-alkyl and —SO$_2$—$C_1$-$C_4$-alkyl; and Y is phenyl [sic], pyridine, pyridazine, pyrimidine and pyrazine and $R^4$ is hydrogen, COOR$^9$ and CO-Z in which Z is NR$^{10}$R$^{11}$ and

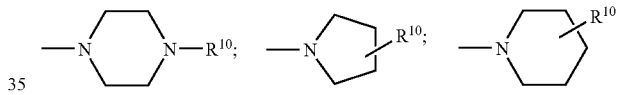

$R^9$ is hydrogen, $C_1$-$C_6$-alkyl, linear or branched, and which may [lacuna] substituted by a phenyl ring which may itself also be substituted by one or two $R^{12}$ radicals, and $R^{10}$ is hydrogen, $C_1$-$C_6$-alkyl, linear or branched, and which may [lacuna] substituted by a phenyl ring which itself may also be substituted by one or two $R^{12}$ radicals, and

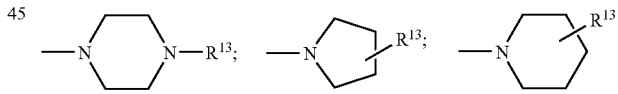

$R^{11}$ is hydrogen, $C_1$-$C_6$-alkyl, branched or unbranched, which may also be and [sic] substituted by a phenyl ring which may also carry an $R^9$ radical, and $R^{12}$ can be hydrogen, $C_1$-$C_4$-alkyl, branched or unbranched, —O—$C_1$-$C_4$-alkyl, OH, Cl, F, Br, I, CF$_3$, NO$_2$, NH$_2$, CN, COOH, COO—$C_1$-$C_4$-alkyl, —NHCO—$C_1$-$C_4$-alkyl, —NHCO-phenyl, —NHSO$_2$—$C_1$-$C_4$-alkyl, —NHSO$_2$-phenyl, —SO$_2$—$C_1$-$C_4$-alkyl and —SO$_2$-phenyl, $R^{13}$ is hydrogen, $C_1$-$C_6$-alkyl, linear or branched, and which may [lacuna] substituted by a phenyl ring which may itself also be substituted by one or two $R^{12}$ radicals, and $R^{14}$ is hydrogen, $C_1$-$C_6$-alkyl, linear or branched, and which may [lacuna] substituted by a phenyl ring which may itself also be substituted by one or two $R^{12}$ radicals, and n is a number 0, 1 or 2, and
m,q is, independently of one another, a number 0, 1, 2, 3 or 4.

Preferred compounds of the general formula I are those in which

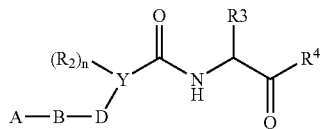

A —$CH_2$—$R^1$, where $R^1$ can be pyrrolidino, piperidino, —$NR^5R^6$ and

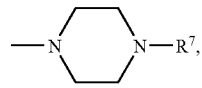

and $R^5$, $R^6$ and $R^7$ can be, independently of one another, hydrogen and $C_1$-$C_4$-alkyl, and
B phenyl [sic]
D —CH=CH—
$R^2$ hydrogen
$R^3$ benzyl, $CH_2CH_2CH_2CH_3$, $CH_2CH_2CH_2CH_2CH_3$ and
Y phenyl [sic] and pyridine and
$R^4$ hydrogen and CO—$NH_2$ and
all the remaining variables have the same meaning as in claim 1.

The compounds of the formula I can be employed as racemates, as enantiomerically pure compounds or as diastereomers. If enantiomerically pure compounds are required, these can be obtained, for example, by carrying out a classical racemate resolution with the compounds of the formula I or their intermediates using a suitable optically active base or acid. On the other hand, the enantiomeric compounds can likewise be prepared by using commercially purchasable compounds, for example optically active amino acids such as phenylalanine, tryptophan and tyrosine.

The invention also relates to compounds which are mesomers or tautomers of compounds of the formula I, for example those in which the aldehyde or keto group in formula I is in the form of an enol tautomer.

The invention further relates to the physiologically tolerated salts of the compounds I which can be obtained by reacting compounds I with a suitable acid or base. Suitable acids and bases are listed, for example, in Fortschritte der Arzneimittelforschung, 1966, Birkhäuser Verlag, Vol. 10, pp. 224-285. These include, for example, hydrochloric acid, citric acid, tartaric acid, lactic acid, phosphoric acid, methanesulfonic acid, acetic acid, formic acid, maleic acid, fumaric acid etc., and sodium hydroxide, lithium hydroxide, potassium hydroxide and tris.

Amides I according to the invention with an aldehyde group can be prepared in various ways, as outlined in synthesis scheme 1.

Synthesis scheme 1

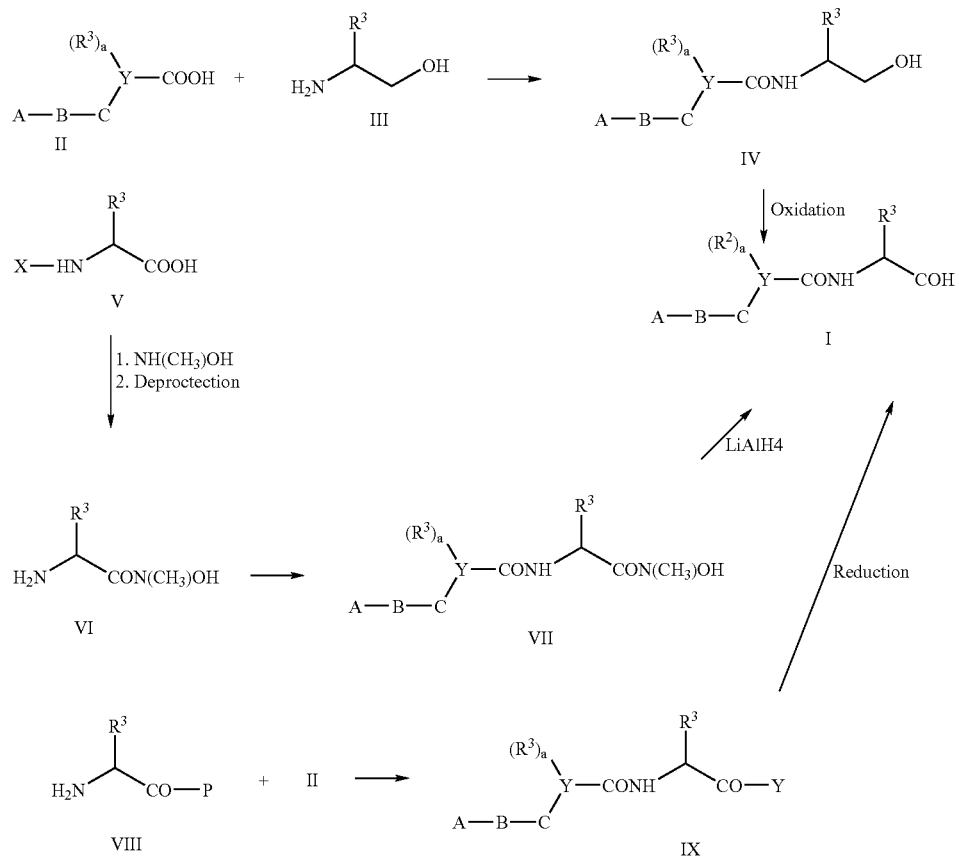

Heterocyclic carboxylic acids II are linked to suitable amino alcohols III to give the corresponding amides IV. Conventional peptide coupling methods are used for this, as detailed either in C. R. Larock, Comprenhensive [sic] Organic Transformations, VCH Publisher, 1989, page 972 et seq., or in Houben-Weyl, Methoden der organischen Chemie, 4th edition, E5, Chapter V. It is preferred to use "activated" acid derivatives of II, with the acid group COOH being converted into a group COL. L is a leaving group such as, for example, Cl, imidazole and N-hydroxybenzotriazole. This activated acid is then reacted with amines to give the amides IV. The reaction takes place in anhydrous inert solvents such as methylene chloride, tetrahydrofuran and dimethylformamide at temperatures from −20 to +25° C. These alcohol derivatives IV can be oxidized to the aldehyde derivatives I according to the invention. Various conventional oxidation reactions can be used for this (see C. R. Larock, Comprenhensive [sic] Organic Transformations, VCH Publisher, 1989, page 604 et seq.) such as, for example, Swern and Swern-analogous oxidations (T. T. Tidwell, Synthesis, 1990, 857-70), sodium hypochloride [sic]/TEMPO (S. L. Harbenson et al., see above) or Dess-Martin (J. Org. Chem. 1983, 48, 4155). Preferably used for this are inert aprotic solvents such as dimethylformamide, tetrahydrofuran or methylene chloride with oxidizing agents such as DMSO/pyxSO$_3$ or DMSO/oxalyl chloride at temperatures from −50 to +25° C., depending on the method (see above literature).

Alternatively, the carboxylic acid II can be reacted with amino hydroxamic acid derivatives VI to give benzamides VII. The reaction in this case is carried out in the same way as for preparing IV. The hydroxamic derivatives VI can be obtained from the protected amino acids V by reaction with a hydroxylamine. An amide preparation process already described is also used in this case. Elimination of the protective group X, for example Boc, takes place in a normal way, for example with trifluoroacetic acid. The amide hydroxamic acids VII obtained in this way can be converted by reduction into the aldehydes I according to the invention. The reducing agent used for this is, for example, lithium aluminum hydride at temperatures from −60 to 0° C. in inert solvents such as tetrahydrofuran or ether. Carboxylic acids or acid derivatives such as esters IX (P=COOR', COSR') can also be prepared in analogy to the last process and can likewise be converted by reduction into the aldehydes I according to the invention. These processes are listed in R. C. Larock, Comprehensive Organic Transformations, VCH Publisher, 1989, pages 619-26.

The amides I according to the invention, which have heterocyclic substituents and have a keto amide or keto ester group, can be prepared in various ways which have been outlined in synthesis schemes 2 and 3.

The carboxylic esters IIa are converted where appropriate with acids or bases such as lithium hydroxide, sodium hydroxide or potassium hydroxide in aqueous medium or in mixtures of water and organic solvents such as alcohols or tetrahydrofuran at room temperature or elevated temperatures, such as 25-100° C., into the acids II.

These acids II are linked to an α-amino acid derivative using customary conditions which are listed, for example, in Houben-Weyl, Methoden der organischen Chemie, 4th edition, E5, Chapter V, and C. R. Larock, Comprehensive Organic Transformations, VCH Publisher, 1989, Ch. 9.

For example, the carboxylic acids II are converted into the "activated" acid derivatives IIb (COOH→COL), where L is a leaving group such as Cl, imidazole and N-hydroxyben zotriazole, and then converted into the derivative XI by adding an amino acid derivative H$_2$N—CH(R$^3$)—COOR. This reaction takes place in anhydrous inert solvents such as methylene chloride, tetrahydrofuran and dimethylformamide at temperatures from −20 to +25° C.

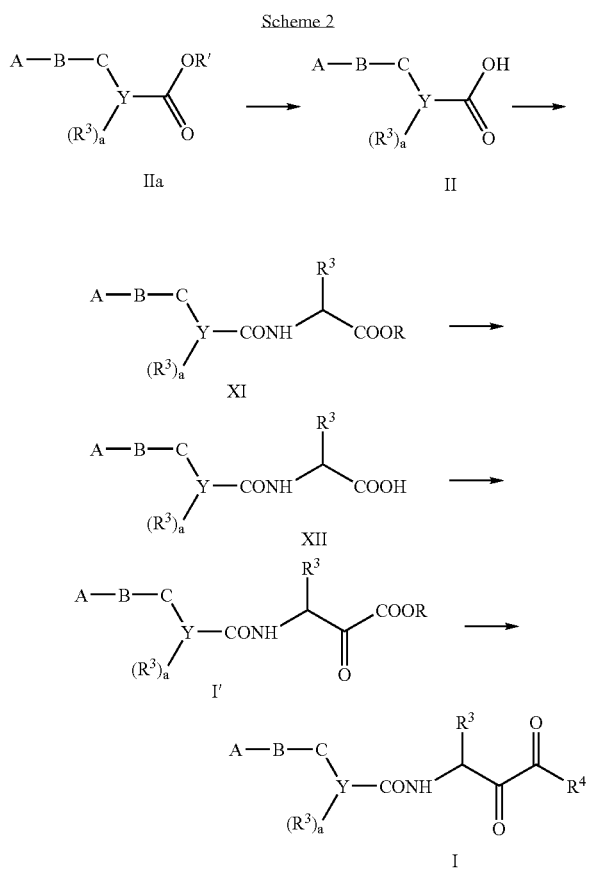

Scheme 2

The derivatives XI, which are usually esters, are converted into the keto carboxylic acids XII by hydrolysis analogous to that described above. The keto esters I' are prepared in a Dakin-West-analogous reaction using a method of ZhaoZhao Li et al., J. Med. Chem., 1993, 36, 3472-80. This entails a [sic] carboxylic acids such as XII being reacted with oxalic monoester chloride at elevated temperature (50-100° C.) in solvents such as, for example, tetrahydrofuran, and the product obtained in this way then being reacted with bases such as sodium ethanolate in ethanol at temperatures of 25-80° C. to give the keto ester I' according to the invention. The keto esters I' can be hydrolyzed as described above for example to keto carboxylic acids according to the invention.

The reaction to give keto benzamides I' likewise takes place in analogy to the method of ZhaoZhao Li et al. (see above). The keto group in I' is protected by adding 1,2-ethanedithiol with Lewis acid catalysis, such as, for example, boron trifluoride etherate, in inert solvents such as methylene chloride at room temperature, resulting in a dithiane. These derivatives are reacted with amines R$^3$—H in polar solvents such as alcohols at temperatures of 0-80° C., resulting in the keto amides I (R$^4$=Z or NR$^{10}$R$^{11}$).

Scheme 3

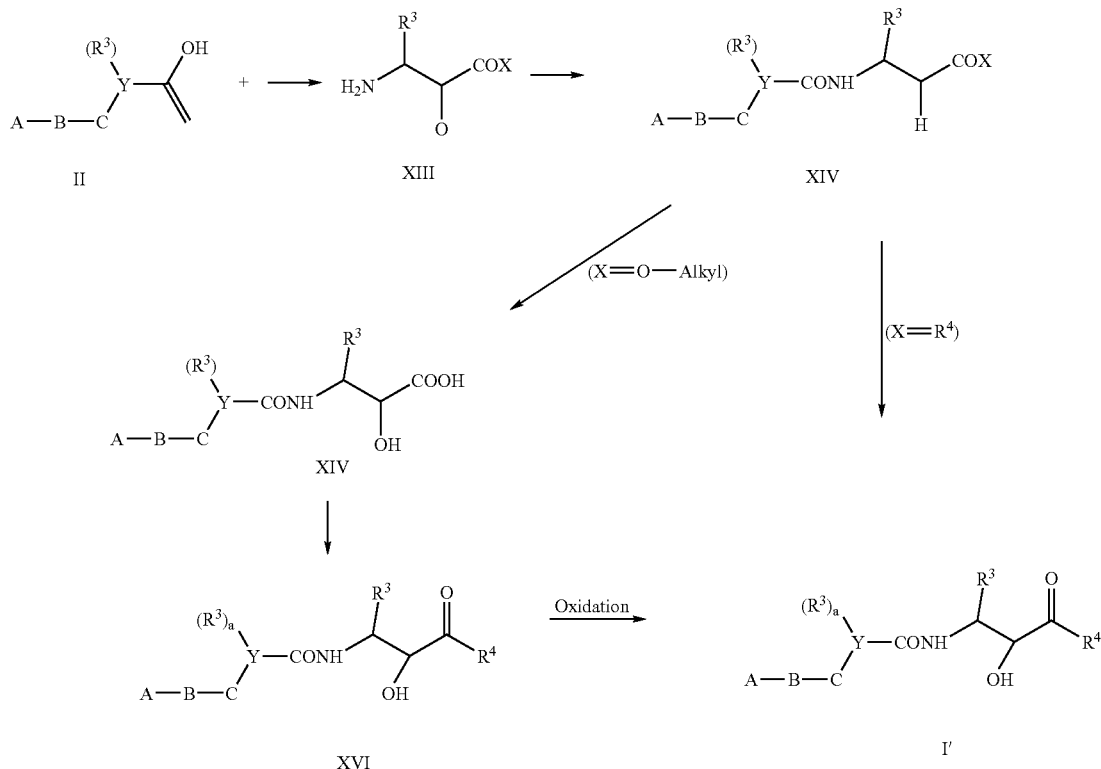

An alternative method is depicted in scheme 3. The keto carboxylic acids II are reacted with amino hydroxy carboxylic acid derivatives XIII (for preparation of XIII, see S. L. Harbenson et al., J. Med. Chem. 1994, 37, 2918-29 or J. P. Burkhardt et al. Tetrahedron Lett. 1988, 29, 3433-3436) using customary peptide coupling methods (see above, Houben-Weyl), resulting in amides XIV. These alcohol derivatives XIV can be oxidized to the keto carboxylic acid derivatives I according to the invention. It is possible to use for this various customary oxidation reactions (see C. R. Larock, Comprehensive Organic Transformations, VCH Publisher, 1989, page 604 et seq.) such as, for example, Swern and Swern-analogous oxidations, preferably dimethyl sulfoxide/pyridine-sulfur trioxide complex in solvents such as methylene chloride or tetrahydrofuran, where appropriate with the addition of dimethyl sulfoxide, at room temperature or temperatures from −50 to 25° C. (T. T. Tidwell, Synthesis 1990, 857-70) or sodium hypochloride [sic]/TEMPO (S. L. Harbenson et al., see above).

In the case of α-hydroxy esters XIV (X=O-alkyl), these can be hydrolyzed to carboxylic acids XV using methods analogous to those above, but preferably using lithium hydroxide in water/tetrahydrofuran mixtures at room temperature. Other esters or amides XVI are prepared by reaction with alcohols or amines under coupling conditions described above. The alcohol derivative XVI can be oxidized to give keto carboxylic acid derivatives I according to the invention.

The preparation of the carboxylic esters II have [sic] already been described for some instances, or it takes place by usual chemical methods.

Compounds in which C is a bond are prepared by conventional aromatic coupling, for example Suzuki coupling with boric acid derivatives and halides with palladium catalysis or copper-catalyzed coupling of aromatic halides. The alkyl-bridged radicals (C=$(CH_2)_m$—) can be prepared by reducing the analogous ketones or by alkylating the organolithium, e.g. orthophenyloxazolidines, or other organometallic compounds (cf. I. M. Dordor et al., J. Chem. Soc. Perkins Trans. I, 1984, 1247-52).

Ether-bridged derivatives are prepared by alkylating the corresponding alcohols or phenols with halides. Alkene- and alkyne-bridged compounds are prepared, for example, by the Heck reaction from aromatic halides and corresponding alkenes and alkynes (cf. I. Sakamoto et al., Chem. Pharm. Bull., 1986, 34, 2754-59).

The amides I with heterocyclic substituents of the present invention are inhibitors of cysteine proteases, especially cysteine proteases such as calpains I and II and cathepsins B and L.

The inhibitory effect of the amides I with heterocyclic substituents has been determined using enzyme assays known from the literature, determining as criterion of effect a concentration of the inhibitor at which 50% of the enzyme activity is inhibited (=$IC_{50}$). The amides I were measured in this way for their inhibitory effect on calpain I, calpain II and cathepsin B.

Cathepsin B Assay

The inhibition of cathepsin B was determined by a method analogous to that of S. Hasnain et al., J. Biol. Chem., 1993, 268, 235-40.

2 µl of an inhibitor solution prepared from inhibitor and DMSO (final concentrations: 100 µM to 0.01 µM) are [lacuna] to 88 µl of cathepsin B (cathepsin B from human liver (Calbiochem), diluted to 5 units in 500 µM buffer). This mixture is preincubated at room temperature (25° C.) for 60 minutes and then the reaction is started by adding 10 µM of 10 mM Z-Arg-Arg-pNA (in buffer with 10% DMSO). The reaction is followed in a microtiter plate reader at 405 mM [sic] for 30 minutes. The $IC_{50}$s are then determined from the maximum gradients.

Calpain I and II Assay

The testing of the inhibitory properties of calpain inhibitors takes place in buffer with 50 mM tris-HCl, pH 7.5; 0.1 M NaCl; 1 mM dithiotreithol [sic]; 0.11 mM $CaCl_2$, using the fluorogenic calpain substrate Suc-Leu-Tyr-AMC (25 mM dissolved in DMSO, Bachem/Switzerland). Human µ-calpain is isolated from erythrocytes, and enzyme with a purity >95%, assessed by SDS-PAGE, Western blot analysis and N-terminal sequencing, is obtained after more [sic] chromatographic steps (DEAE-Sepharose, phenyl-Sepharose, Superdex 200 and blue Sepharose). The fluorescence of the cleavage product 7-amino-4-methylcoumarin (AMC) is followed in a Spex Fluorolog fluorimeter at $\lambda ex=380$ nm and $\lambda em=460$ nm. The cleavage of the substrate is linear in a measurement range of 60 min., and the autocatalytic activity of calpain is low, if the tests are carried out at temperatures of 12° C. The inhibitors and the calpain substrate are added to the test mixture as DMSO solutions, and the final concentration of DMSO ought not to exceed 2%.

In a test mixture, 10 µl of substrate (250 µM final) and then 10 µl of µ-calpain (2 µg/ml final, i.e. 18 nM) are added to a 1 ml cuvette containing buffer. The calpain-mediated cleavage of the substrate is measured for 15 to 20 min. Then 10 µl of inhibitor (50 to 100 µM solution in DMSO) are added and the inhibition of cleavage is measured for a further 40 min.

$K_i$ values are determined using the classical equation for reversible inhibition:

$Ki=I(v0/vi)-1$; where I=inhibitor concentration, v0=initial rate before addition of the inhibitor; vi=reaction rate at equilibrium.

The rate is calculated from v=AMC liberation/time, i.e. height/time.

Calpain is an intracellular cysteine protease. Calpain inhibitors must pass through the cell membrane in order to prevent intracellular proteins being broken down by calpain. Some known calpain inhibitors, such as, for example, E 64 and leupeptin, cross cell membranes only poorly and accordingly show only a poor effect on cells, although they are good calpain inhibitors. The aim is to find compounds better able to cross membranes. Human platelets are used to demonstrate the ability of calpain inhibitors to cross membranes.

Calpain-mediated breakdown of tyrosine kinase pp60src in platelets

Tyrosine kinase pp60src is cleaved by calpain after activation of platelets. This has been investigated in detail by Oda et al. in J. Biol. Chem., 1993, 268, 12603-12608. This revealed that the cleavage of pp60src can be prevented by calpeptin, a calpain inhibitor. The cellular efficacy of our substances was tested based on this publication. Fresh, citrated, human blood was centrifuged at 200 g for 15 min. The platelet-rich plasma was pooled and diluted 1:1 with platelet buffer (platelet buffer: 68 mM NaCl, 2.7 mM KCl, 0.5 mM $MgCl_2 \times 6\ H_2O$, 0.24 mM $NaH_2PO_4 \times H_2O$, 12 mM $NaHCO_3$, 5.6 mM glucose, 1 mM EDTA, pH 7.4). After a centrifugation step and washing step with platelet buffer, the platelets were adjusted to $10^7$ cells/ml. The human platelets were isolated at RT.

In the assay mixture, isolated platelets ($2 \times 10^6$) were preincubated with various concentrations of inhibitors (dissolved in DMSO) at 37° C. for 5 min. The platelets were then activated with 1 µM ionophore A23187 and 5 mM $CaCl_2$. After incubation for 5 min., the platelets were briefly centrifuged at 13000 rpm, and the pellet was taken up in SDS sample buffer (SDS sample buffer: 20 mM tris-HCl, 5 mM EDTA, 5 mM EGTA, 1 mM DTT, 0.5 mM PMSF, 5 µg/ml leupeptin, 10 µg/ml pepstatin, 10% glycerol and 1% SDS). The proteins were fractionated in a 12% gel, and pp60src and its 52 kDa and 47 kDa cleavage products were identified by Western blotting. The polyclonal rabbit antibody used, anti-Cys-src ($pp60^{c-rc}$) was purchased from Biomol Feinchemikalien (Hamburg). This primary antibody was detected using a second, HRP-coupled goat antibody (Boehringer Mannheim, FRG). The Western blotting was carried out by known methods.

The cleavage of pp60src was quantified by densitometry, using as controls unactivated (control 1: no cleavage) and ionophore- and calcium-treated platelets (control 2: corresponds to 100% cleavage). The $ED_{50}$ corresponds to the concentration of inhibitor at which the intensity of the color reaction is reduced by 50%.

Glutamate-Induced Cell Death in Cortical Neurones

The test was carried out as in Choi D. W., Maulucci-Gedde M. A. and Kriegstein A. R., "Glutamate neurotoxicity in cortical cell culture". J. Neurosci. 1989 [sic], 7, 357-368. The cortex halves were dissected out of 15-day old mouse embryos and the single cells were obtained enzymatically (trypsin). These cells (glia and cortical neurones) are seeded out in 24-well plates. After three days (laminin-coated plates) or seven days (ornithine-coated plates), the mitosis treatment is carried out with FDU (5-fluoro-2deoxyuridines). 15 days after preparation of the cells, cell death is induced by adding glutamate (15 minutes). After removal of glutamate, the calpain inhibitors are added. 24 hours later, the cell damage is estimated by determining lactate dehydrogenase (LDH) in the cell culture supernatant.

It is postulated that calpain is also involved in apoptotic cell death (M. K. T. Squier et al., J. Cell. Physiol. 1994, 159, 229-237; T. Patel et al. Faseb Journal 1996, 590, 587-597).

For this reason, in another model, cell death was induced in a human cell line with calcium in the presence of a calcium ionophore. Calpain inhibitors must get inside the cell and inhibit calpain there in order to prevent the induced cell death.

Calcium-Mediated Cell Death in NT2 Cells

Cell death can be induced in the human cell line NT2 by calcium in the presence of the ionophore A 23187. $10^5$ cells/well were plated out in microtiter plates 20 hours before the test. After this period, the cells were incubated with various concentrations of inhibitors in the presence of 2.5 µM ionophore and 5 mM calcium. 0.05 ml of XTT (Cell Proliferation Kit II, Boehringer Mannheim) was added to the reaction mixture after 5 hours. The optical density is determined approximately 17 hours later, in accordance with the manufacturer's information, in an SLT Easy Reader EAR 400. The optical density at which half the cells have died is calculated from the two controls with cells without inhibitors incubated in the absence and presence of ionophore.

Elevated glutamate activities occur in a number of neurological disorders or psychological disturbances and lead to states of overexcitation or toxic effects in the central nervous system (CNS). The effects of glutamate are mediated by various receptors. Two of these receptors are classified, in accordance with the specific agonists, as NMDA receptor and AMPA receptor. Antagonists to these glutamate-mediated effects can thus be employed for treating these disorders, in particular for therapeutic use for neurodegenerative disorders such as Huntington's chorea and Parkinson's disease, neurotoxic impairments after hypoxia, anoxia, ischemia and after lesions like those occurring after stroke and trauma, or else as antiepileptics (cf. Arzneim. Forschung 1990, 40, 511-514; TIPS, 1990, 11, 334-338; Drugs of the Future 1989, 14, 1059-1071).

Protection from Cerebral Overexcitation by Excitatory Amino Acids (NMDA and AMPA Antagonism in Mice)

Intracerebral administration of excitatory amino acids (EAA) induces such drastic overexcitation that it leads to convulsions and death of the animals (mice) within a short time. These signs can be inhibited by systemic, e.g. intraperitoneal, administration of centrally acting substances (EAA antagonists). Since excessive activation of EAA receptors in the central nervous system plays a significant part in the pathogenesis of various neurological disorders, it is possible to infer from the detected EAA antagonism in vivo that the substances may have therapeutic uses for such CNS disorders. As a measure of the efficacy of the substances, an $ED_{50}$ was determined, at which 50% of the animals are free of signs, owing to the previous i.p. administration of the measured substance, by a fixed dose of either NMDA or AMPA.

The amides I with heterocyclic substituents are inhibitors of cysteine derivatives [sic] like calpain I and II and cathepsin B and L, and can thus be used to control diseases associated with an elevated activity of calpain enzymes or cathepsin enzymes. The present amides I can accordingly be used to treat neurodegenerative disorders occurring after ischemia, damage due to reperfusion after vascular occlusions, trauma, subarachnoid hemorrhages and stroke, and neurodegenerative disorders such as multi-infarct dementia, Alzheimer's disease, Huntington's disease and epilepsies and, in addition, to treat damage to the heart after cardiac ischemias, damage to the kidneys after renal ischemia, skeletal muscle damage, muscular dystrophies, damage caused by proliferation of smooth muscle cells, coronary vasospasms, cerebral vasospasms, cataracts of the eyes, restenosis of the blood vessels after angioplasty. In addition, the amides I may be useful in the chemotherapy of tumors and metastasis thereof and for treating disorders in which an elevated interleukin-1 level occurs, such as inflammation and rheumatic disorders.

The pharmaceutical preparations according to the invention comprise a therapeutically effective amount of the compounds I in addition to conventional pharmaceutical ancillary substances.

The active ingredients can be present in the usual concentrations for local external use, for example in dusting powders, ointments or sprays. As a rule, the active ingredients are present in an amount of from 0.001 to 1% by weight, preferably 0.001 to 0.1% by weight.

For internal use, the preparations are administered in single doses. From 0.1 to 100 mg are given per kg of body weight in a single dose. The preparation may be administered in one or more doses each day, depending on the nature and severity of the disorders.

The pharmaceutical preparations according to the invention comprise, apart from the active ingredient, the customary excipients and diluents appropriate for the required mode of administration. For local external use it is possible to use pharmaceutical ancillary substances such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Suitable examples for internal use are lactose, propylene glycol, ethanol, starch, talc and polyvinylpyrrolidone.

It is also possible for antioxidants such as tocopherol and butylated hydroxyanisole, and butylated hydroxytoluene, flavor-improving additives, stabilizers, emulsifiers and lubricants to be present.

The substances which are present in the preparation in addition to the active ingredient, and the substances used in producing the pharmaceutical preparations, are toxicologically acceptable and compatible with the active ingredient in each case. The pharmaceutical preparations are produced in a conventional way, for example by mixing the active ingredient with other customary excipients and diluents.

The pharmaceutical preparations can be administered in various ways, for example orally, parenterally, such as intravenously by infusion, subcutaneously, intraperitoneally and topically. Thus, possible presentations are tablets, emulsions, solutions for infusion and injection, pastes, ointments, gels, creams, lotions, dusting powders and sprays.

EXAMPLES

Example 1

(S)-2-(E-2-(4-(N,N-Dimethylaminomethyl)phenyl)ethen-1-yl)-N-(3-phenylpropan-1-al-2-yl)benzamide [sic]

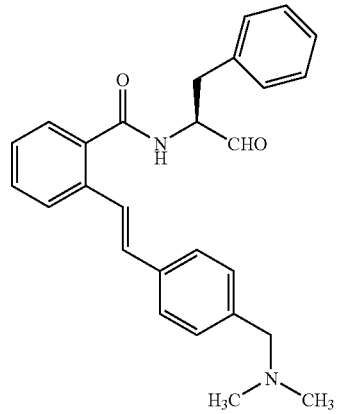

a) Ethyl 2-(E-2-(4-(N,N-dimethylaminomethyl)phenyl)ethen-1-yl)benzoate 18.8 g (82 mmol) of ethyl 2-bromobenzoate, 17.2 g (107 mmol) of 4-(N,N,-dimethylaminomethyl)styrene [sic], 20.7 g (205 mmol) of triethylamine, 0.36 g of palladium(II) acetate and 0.96 g of tri(o-tolyl)phosphine were mixed in 200 ml of dimethylformamide and, after addition of 1 ml of water, stirred at 140° C. for 3 h. The reaction mixture was then concentrated in vacuo, and the resulting residue was partitioned between ethyl acetate and water. The organic phase was separated off, washed with water, dried and concentrated in vacuo. The residue was then recrystallized from petroleum ether. 16.1 g (63%) of the product were obtained.

b) 2-(E-2-(4-(N,N-Dimethylaminomethyl)phenyl)ethen-1-yl)-benzoic acid 15.5 g (50 mmol) of the intermediate 1a were dissolved in 150 ml of ethanol, and 50 ml of 2M sodium hydroxide solution were added. The mixture was stirred at room temperature for 16 h. The solution was then neutralized with 2M hydrochloric acid, and the ethanol was removed in vacuo. The resulting precipitate was filtered off with suction and dried. 13.6 g (97%) of the product were obtained.

c) (S)-2-(E-2-(4-(N,N-Dimethylaminomethyl)phenyl)ethen-1-yl)-N-(3-phenylpropan-1-ol-2-yl)benzamide [sic]

1.97 g (7 mmol) of the intermediate 1b and 1.06 g (7 mmol) of (S)-phenylalaninol were mixed in 25 ml of methylene chloride, and 1.77 g (17.5 mmol) of triethylamine and 0.95 g (7 mmol) of 1-hydroxybenzotriazole were added. Then, at 0° C., 1.34 g (7 mmol) of 1-ethyl-3-(dimethylaminopropyl)carbodiimide hydrochloride were added, and the mixture was stirred at 0° C. for 1 h and then at room temperature for 16 h. The reaction mixture was washed successively with 100 ml of 5% strength citric acid and 100 ml of sodium bicarbonate solution and, after drying, concentrated in vacuo. 2.63 g (88%) of the product were obtained.

d) (S)-2-(E-2-(4-N,N-Dimethylaminomethyl)phenyl)ethen-1-yl)-N-(3-phenylpropan-1-al-2-yl)benzamide [sic]

2.40 g (5.6 mmol) of intermediate 1c and 2.27 g (22.4 mmol) of triethylamine were dissolved in 25 ml of dry dimethyl sulfoxide, and 3.57 g (22.4 mmol) of pyridine/sulfur trioxide complex were added. The mixture was stirred at room temperature for 16 h. The mixture was then added to aqueous sodium bicarbonate solution, and the precipitate was filtered off with suction. The aqueous phase was extracted with ethyl acetate, which was then dried and concentrated in vacuo. This residue was combined with the first precipitate. 1.57 g (68%) of the product were obtained. $^1$H-NMR (D$_6$-DMSO): δ=2.4 (6H), 2.8-3.1 (2H), 3.8 (1H), 7.0-7.7 (14H), 7.8 (1H), 8.8 (1H) and 9.75 (1H) ppm.

EXAMPLE 2

(S)-2-(E-2-(4-(N,N-Dimethylaminomethyl)phenyl)ethen-1-yl)-N-(3-phenylpropan-1-al-2-yl)nicotinamide [sic]

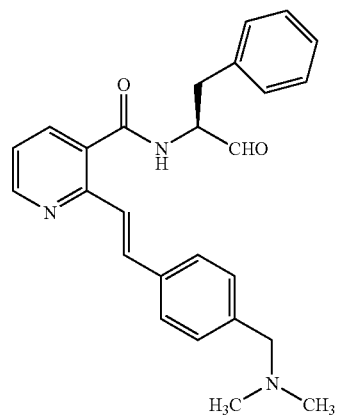

a) Ethyl 2-(E-2-(4-(N,N-dimethylaminomethyl)phenyl)ethen-1-yl)nicotinate 6.7 g (39 mmol) of ethyl 2-chloronicotinate, 8.2 g (51 mmol) of 4-(N,N-dimethylaminomethyl)styrene, 9.9 g (98 mmol) of triethylamine, 0.36 g of palladium(II) acetate and 0.96 [lacuna] of tri(o-tolyl)phosphine were mixed in 150 ml of dimethylformamide and, after addition of 1 ml of water, stirred at 140° C. for 13 h. The reaction mixture was then concentrated in vacuo, and the resulting residue was partitioned between ethyl acetate and water. The organic phase was separated off, washed with water, dried and concentrated in vacuo. The residue was then crystallized as oxalate from isopropanol after addition of an equivalent amount of oxalic acid. 4.1 g (27%) of the product were obtained as monooxalate.

b) 2-(E-2-(4-N,N-Dimethylaminomethyl)phenyl)ethen-1-yl)-nicotinic acid 3.9 g (10 mmol) of the intermediate 2a were added to 100 ml of ethanol/tetrahydrofuran (1/1), and 25 ml of 2M sodium hydroxide solution were added. The mixture was stirred at room temperature for 16 h. The reaction solution was then neutralized with 2M hydrochloric acid, and the ethanol was removed in vacuo. The resulting precipitate was filtered off with suction and dried. 2.46 g (87%) of the product were obtained.

c) (S)-2-(E-2-(4-N,N-Dimethylaminomethyl)phenyl)ethen-1-yl)-N-(3-phenylpropan-1-ol-2-yl)nicotinmide [sic]

2.03 g (7.2 mmol) of the intermediate 2b and 1.09 g (7.2 mmol) of (S)-phenylalaninol were added to 25 ml of methylene chloride, and 1.82 g (18 mmol) of triethylamine and 0.97 g (7.2 mmol) of 1-hydroxybenzotriazole were added. Then, at 0° C., 1.38 g (7.2 mmol) of 1-ethyl-3-(dimethylaminopropyl)carbodiimide hydrochloride were added, and the mixture was stirred at 0° C. for 1 h and then at room temperature for 16 h. The reaction mixture was washed successively with 100 ml of 5% strength citric acid and 100 ml of sodium bicarbonate solution and, after drying, concentrated in vacuo. 2.45 g (82%) of the product were obtained.

d) (S)-2-(E-2-(4-N,N-Dimethylaminomethyl)phenyl)-ethen-1-yl)-N-(3-phenylpropan-1-al-2-yl))nicotinamide [sic]

2.27 g (5.5 mmol) of the intermediate 2c and 2.21 g (21.85 mmol) of triethylamine were dissolved in 25 ml of dry dimethyl sulfoxide, and 3.48 g (21.85 mmol) of pyridine/sulfur trioxide complex were added. The mixture was stirred at room temperature for 16 h. The reaction mixture was then added to aqueous sodium bicarbonate solution, and the precipitate was filtered off with suction. The aqueous phase was extracted with ethyl acetate, which was then dried and concentrated in vacuo. This residue was combined with the first precipitate. 1.4 g (61%) of the product were obtained.

H-NMR ($D_6$-DMSO): δ=2.15 (6H), 2.8 (1H), 3.3 (1H), 4.7 (1H), 6.9-7.8 (13H), 8.6 (1H), 9.0 (1H) and 9.7 (1H) ppm.

Example 3

N-(1-Carbamoyl-1-oxo-3-phenylpropan-2-yl)-2-(E-2-(4-(morpholin-1-ylmethyl)phenyl)ethen-1-yl)benzamide [sic]

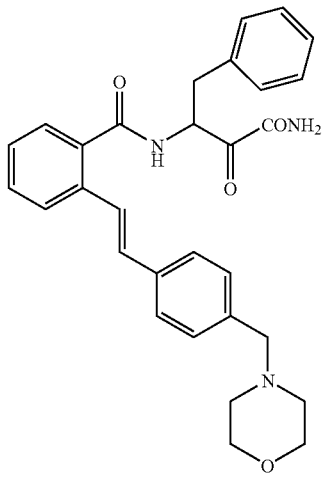

a) N-(4-Vinylphenyl)methylmorpholine 20 ml (0.14 mol) of 4-vinylbenzylchloride and 25 ml (0.28 mol) of morpholine were refluxed in 150 ml of methanol for 3 h. The mixture was then concentrated in vacuo, and the resulting residue was partitioned between 1M hydrochloric acid and water [sic]. The acidic phase was washed with ether and then made alkaline with 2M sodium hydroxide solution. This aqueous phase was extracted with ether. This organic phase was dried and concentrated in vacuo, resulting in 24.6 g of the product.

b) Ethyl E-2-(4-(morpholin-1-ylmethyl)phenyl)ethen-1-yl-benzoate [sic]

14 g (68.9 mmol) of the intermediate 3a, 16.6 g (72.3 mmol) of ethyl 2-bromobenzoate, 24 ml (172 mmol) of triethylamine, 0.36 g of palladium(II) chloride, 0.96 g of tri-o-tolylphosphine and 1 ml of water were heated in 150 ml of dimethylformamide at 100° C. for 2 h. The mixture was then poured into water and the resulting solution was extracted with diethyl ether. The organic phase was dried and then concentrated in vacuo, resulting in 28 g of the product.

c) E-2-(4-(Morpholin-1-ylmethyl)phenyl)ethen-1-yl-benzoic acid x hydrochloride [sic]

28 g (80 mmol) of the intermediate 3b were dissolved [lacuna] 250 ml of ethanol, and 9 g (159 mmol) of potassium hydroxide dissolved in 150 ml of water were added. The mixture was stirred at room temperature for 16 h. The mixture was then neutralized with hydrochloric acid and extracted with ethyl acetate. The organic phase was dried and concentrated in vacuo. The residue was dissolved in ethanol, and the hydrochloride was precipitated by adding ethanolic hydrogen chloride solution and was then filtered off with suction. 24.3 g of the product were obtained.

d) N-(1-Carbamoyl-1-hydroxy-3-phenylpropan-2-yl)-2-(E-2-(4-(morpholin-1-ylmethyl)phenyl)ethen-1-yl)benzamide [sic]

1 g (2.8 mmol) of the intermediate 3c were reacted in analogy to method 2c with 3-amino-2-hydroxy-4-phenylbutyramide (J. P. Burkhardt et al., Tetrahedon [sic] Lett. 1988, 3433-3436), resulting in 0.97 g of the product.

e) N-(1-Carbamoyl-1-oxo-3-phenylpropan-2-yl)-2-(E-2-(4-(morpholin-1-ylmethyl)phenyl)ethen-1-yl)benzamide [sic]

0.9 g (1.8 mmol) of intermediate 3d and 1 μL (7.2 mmol) of triethylamine were dissolved in 20 ml of anhydrous dimethyl sulfoxide. Then, at room temperature, 0.57 g (3.6 mmol) of pyridine/sulfur trioxide complex dissolved in 12 ml of anhydrous dimethyl sulfoxide was added dropwise. The mixture was stirred for 30 minutes. The mixture was then poured into water and neutralized with aqueous sodium bicarbonate solution. The aqueous phase was extracted with ethyl acetate. The organic phase was then dried and concentrated in vacuo. The residue was precipitated from acetone/ether, with 0.51 g of the product precipitating.

$^1$H-NMR ($D_6$-DMSO): δ=2.3 (4H), 2.9 (1H), 3.25 (1H), 3.5 (2H), 3.6 (2H), 5.3 (1H), 7.0-7.6 (13H), 7.8 (2H), 8.1 (1H) and 8.9 (1H) ppm.

The following examples were prepared in analogy to the above examples and methods:

Example 4

N-(1-Carbamoyl-1-oxo-3-phenylpropan-2-yl)-2-(E-2-(4-(1-pyrrolidinylmethyl)phenyl)ethen-1-yl)benzamide [sic]

$^1$H-NMR ($CF_3COOH$): δ=2.15 (6H), 2.8 (2H), 3.3 (1H), 4.7 (1H), 6.9-7.8 (13H), 8.6 (1H), 9.0 (1H) and 9.7 (1H) ppm.

Example 5

N-(1-Carbamoyl-1-oxo-3-phenylpropan-2-yl)-2-(E-2-(4-(N,N-diethylaminomethyl)phenyl)ethen-1-yl)benzamide [sic]

$^1$H-NMR (D$_6$-DMSO): δ=1.0 (6H), 2.5 (4H), 2.9 (1H), 3.25 (1H), 3.5 (2H), 5.4 (1H), 7.1-7.6 (13H), 7.8-7.9 (2H), 8.1 (1H) and 8.9 (1H) ppm.

Example 6

2-(2E-(4-(N,N-Benzylmethylaminomethyl)phenyl)ethen-1-yl)-N-(1-carbamoyl-1-oxo-3-phenylpropan-2-yl)benzamide [sic]

$^1$H-NMR (D$_6$-DMSO): δ=2.1 (3H), 2.9 (1H), 3.1-3.6 (5H), 5.3 (1H), 7.0-8.0 (16H), 8.1 (1H) and 8.9 (1H) ppm.

Example 7

N-(1-Carbamoyl-1-oxo-3-phenylpropan-2-yl)-2-(E-2-(4-(N,N-dimethylaminomethyl)phenyl)ethen-1-yl)benzamide [sic]

$^1$H-NMR (D$_6$-DMSO): δ=2.5 (6H), 2.9 (1H), 3.3 (1H), 3.9 (2H); 5.4 (1H), 7.2-7.6 (15H), 8.9 (1H) and 8.9 (1H) ppm.

Example 8

N-(1-Carbamoyl-1-oxo-3-phenylpropan-2-yl)-2-(E-2-(4-(N,N-di-n-propylaminomethyl)phenyl)ethen-1-yl)benzamide [sic]

$^1$H-NMR (D$_6$-DMSO): δ=0.8 (6H); 1.5 (4H); 2.3 (2H); 2.9 (1H); 3.25 (1H); 3.5 (2H); 5.3 (1H), 7.1-7.5 (13H), 7.8 (2H), 8.1 (1H) and 8.9 (1H) ppm.

Example 9

N-(1-Carbamoyl-1-oxohexan-2-yl)-2-(E-2-(4-(N,N-dimethylaminomethyl)phenyl)ethen-1-yl)benzamide [sic] hydrochloride $^1$H-NMR (D$_6$-DMSO): δ=0.8 (3H); 1.2-1.9 (6H); 2.7 (6H), 4.2 (2H), 5.1 (1H), 7.1-8.0 (11H), 8.05 (1H) and 8.8 (1H) ppm.

Example 10

N-(1-Carbamoyl-1-oxo-3-phenylpropan-2-yl)-2-(E-2-(4-(4-methyl-1-piperazin-1-ylmethyl)phenyl)ethen-1-yl)benzamide x dihydrochloride [sic]

$^1$H-NMR (D$_6$-DMSO): δ=2.8-2.9 (3H), 3.1-3.8 (9H), 4.2 (2H), 5.3 (1H), 7.1-7.9 (17H), 8.1 (1H) and 8.9 (1H) ppm.

Example 11

N-(1-Carbamoyl-1-oxo-3-phenylpropan-2-yl)-2-(E-2-(2-(N,N-dimethylaminomethyl)phenyl)ethen-1-yl)benzamide [sic]

$^1$H-NMR (D$_6$-DMSO): δ=2.1 (6H), 2.9 (1H), 3.2 (1H), 3.5 (1H); 5.3 (1H), 7.0-8.0 (16H), 8.1 (1H) and 8.9 (1H) ppm.

Example 12

N-(1-Carbamoyl-1-oxo-3-phenylpropan-2-yl)-2-(E-2-(4-(N,N-dimethylaminomethyl)phenyl)ethen-1-yl)nicotinamide [sic]

$^1$H-NMR (D$_6$-DMSO): δ=2.3 (6H), 2.85 (1H), 3.2 (1H), 3.7 (1H); 5.4 (1H), 7.2-7.6 (13H), 7.8 (1H), 8.6 (1H) and 9.15 (1H) ppm.

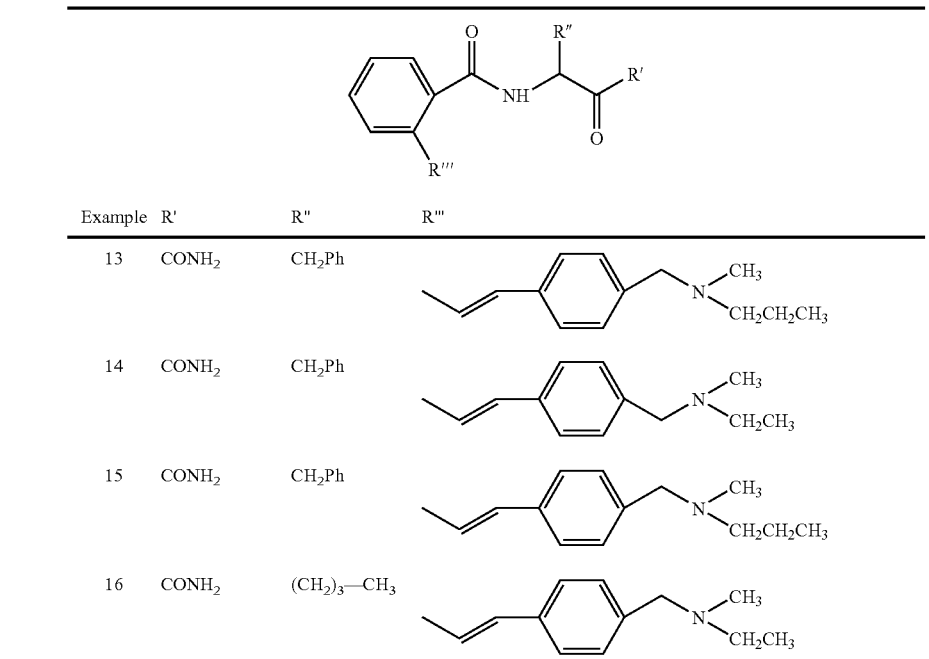

| Example | R' | R" | R''' |
|---|---|---|---|
| 13 | CONH$_2$ | CH$_2$Ph | 4-vinylphenyl-CH$_2$-N(CH$_3$)(CH$_2$CH$_2$CH$_3$) |
| 14 | CONH$_2$ | CH$_2$Ph | 4-vinylphenyl-CH$_2$-N(CH$_3$)(CH$_2$CH$_3$) |
| 15 | CONH$_2$ | CH$_2$Ph | 4-vinylphenyl-CH$_2$-N(CH$_3$)(CH$_2$CH$_2$CH$_3$) |
| 16 | CONH$_2$ | (CH$_2$)$_3$—CH$_3$ | 4-vinylphenyl-CH$_2$-N(CH$_3$)(CH$_2$CH$_3$) |

-continued
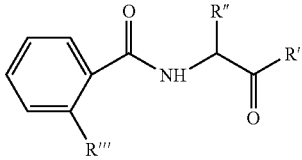
| Example | R' | R" | R''' |
|---|---|---|---|
| 17 | H | CH₂Ph | 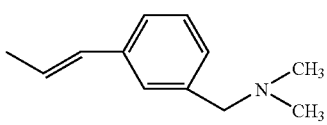 |
| 18 | CONH₂ | CH₂Ph | 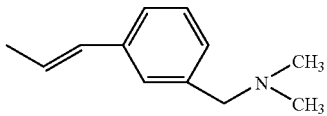 |
| 19 | CONH₂ | CH₂Ph | 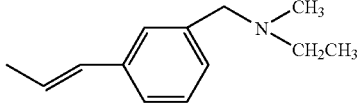 |
| 20 | CONH₂ | CH₂Ph | 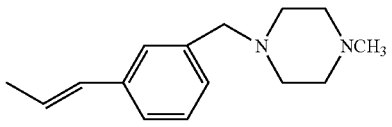 |
| 21 | CONH₂ | (CH₂)₃CH₃ | 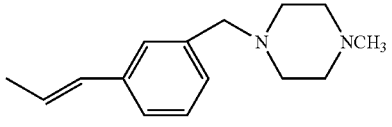 |
| 22 | H | CH₂Ph | 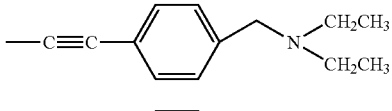 |
| 23 | CONH₂ | CH₂Ph | 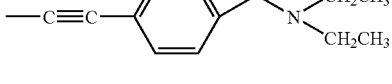 |
| 24 | H | CH₂Ph | 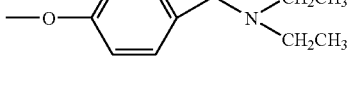 |
| 25 | CONH₂ | (CH₂)₃CH₃ | 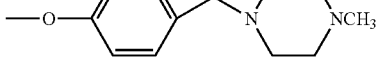 |
| 26 | H | CH₂Ph | 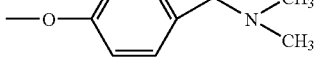 |
| 27 | H | CH₂Ph | 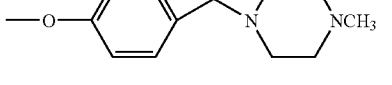 |
| 28 | CONH₂ | CH₂Ph | 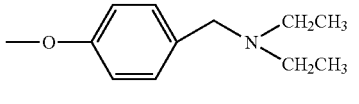 |

-continued

| Example | R' | R'' | R''' |
|---------|-----|------|------|
| 29 | CONH₂ | CH₂Ph | —O—C₆H₄—CH₂—N(CH₃)₂ (4-position) |
| 30 | CONH₂ | (CH₂)₃CH₃ | —O—C₆H₄—CH₂—N(CH₂CH₃)₂ (4-position) |
| 31 | H | CH₂Ph | —CH₂—C₆H₄—CH₂—N(CH₂CH₃)₂ (4-position) |
| 32 | CONH₂ | CH₂Ph | —CH₂—C₆H₄—CH₂—(4-methylpiperazin-1-yl) (4-position) |
| 33 | CONH₂ | CH₂Ph | —CH₂—C₆H₄—CH₂—N(CH₂CH₃)₂ (4-position) |
| 34 | H | CH₂Ph | —CH=CH—C₆H₄—CH₂CH₂—N(CH₃)₂ (4-position) |
| 35 | CONH₂ | CH₂Ph | —CH=CH—C₆H₄—CH₂CH₂—N(CH₃)₂ (4-position) |
| 36 | H | CH₂Ph | —CH=CH—C₆H₄—CH₂CH₂—N(CH₂CH₃)₂ (4-position) |
| 37 | CONH₂ | CH₂Ph | —CH=CH—C₆H₄—CH₂CH₂—N(CH₂CH₃)₂ (4-position) |
| 38 | H | CH₂Ph | —CH=CH—C₆H₄—CH₂CH₂—(4-methylpiperazin-1-yl) (4-position) |
| 39 | CONH₂ | CH₂Ph | —CH=CH—C₆H₄—CH₂CH₂—(4-methylpiperazin-1-yl) (4-position) |
| 40 | H | CH₂Ph | —CH=CH—C₆H₄—CH₂—(pyrrolidin-1-yl) (4-position) |
| 41 | CONH₂ | CH₂Ph | —CH=CH—C₆H₄—CH₂—(pyrrolidin-1-yl) (4-position) |

-continued

| Example | R' | R" | R''' |
|---|---|---|---|
| 42 | H | CH₂Ph | 4-(propenyl)benzyl-piperidine |
| 43 | CONH₂ | CH₂Ph | 4-(propenyl)benzyl-piperidine |
| 44 | CONH₂ | (CH₂)₃CH₃ | 4-(propenyl)benzyl-piperidine |
| 45 | H | (CH₂)₃CH₃ | 4-(propenyl)benzyl-pyrrolidine |
| 46 | CONH₂ | (CH₂)₃CH₃ | 4-(propenyl)benzyl-pyrrolidine |
| 47 | H | (CH₂)₃CH₃ | 4-(propenyl)benzyl-piperidine |
| 48 | H | CH₂Ph | 4-(propenyl)benzyl-N-methylpiperazine |
| 49 | H | CH₂Ph | 4-(propenyl)benzyl-N,N-diethylamine |
| 50 | H | CH₂Ph | 4-(propenyl)benzyl-morpholine |
| 51 | H | (CH₂)₃CH₃ | 4-(propenyl)benzyl-morpholine |
| 52 | CONH₂ | (CH₂)₃CH₃ | 4-(propenyl)benzyl-morpholine |
| 53 | H | CH₂Ph | 4-(propenyl)benzyl-N-methyl-N-ethylamine |
| 54 | H | (CH₂)₃CH₃ | 4-(propenyl)benzyl-N-methyl-N-benzylamine |
| 55 | CONH₂ | (CH₂)₃CH₃ | 4-(propenyl)benzyl-N-methyl-N-benzylamine |

-continued

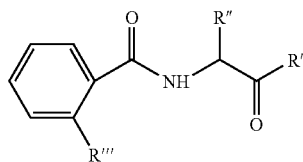

| Example | R' | R'' | R''' |
|---|---|---|---|
| 56 | CONHCH$_2$CH$_3$ | CH$_2$Ph | 4-(4-methylpiperazin-1-ylmethyl)styryl |
| 57 | CONHCH$_2$CH$_3$ | CH$_2$Ph | 4-(N,N-diethylaminomethyl)styryl |
| 58 | CONHCH$_2$CH$_3$ | CH$_2$Ph | 4-(morpholin-4-ylmethyl)styryl |
| 59 | CONHCH$_2$CH$_3$ | CH$_2$Ph | 4-(pyrrolidin-1-ylmethyl)styryl |
| 60 | CONH$_2$ | CH$_2$Ph | 4-(4-ethylpiperazin-1-ylmethyl)styryl |
| 61 | H | CH$_2$Ph | 4-(4-ethylpiperazin-1-ylmethyl)styryl |
| 62 | H | (CH$_2$)$_3$CH$_3$ | 4-(4-ethylpiperazin-1-ylmethyl)styryl |
| 63 | CONH$_2$ | (CH$_2$)$_3$CH$_3$ | 4-(4-ethylpiperazin-1-ylmethyl)styryl |
| 64 | CONH$_2$ | CH$_2$Ph | 4-(4-isopropylpiperazin-1-ylmethyl)styryl |
| 65 | H | CH$_2$Ph | 4-(4-isopropylpiperazin-1-ylmethyl)styryl |
| 66 | H | CH$_2$Ph | 4-(4-phenylpiperazin-1-ylmethyl)styryl |
| 67 | CONH$_2$ | CH$_2$Ph | 4-(4-phenylpiperazin-1-ylmethyl)styryl |
| 68 | H | (CH$_2$)$_3$CH$_3$ | 4-(4-phenylpiperazin-1-ylmethyl)styryl |
| 69 | CONH$_2$ | (CH$_2$)$_3$CH$_3$ | 4-(4-phenylpiperazin-1-ylmethyl)styryl |

-continued
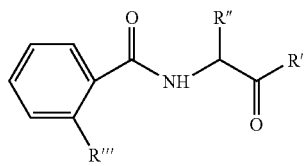
| Example | R' | R" | R''' |
|---|---|---|---|
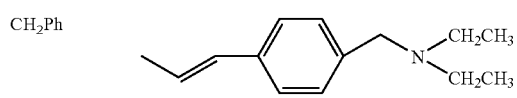
| 70 | H | CH₂Ph | 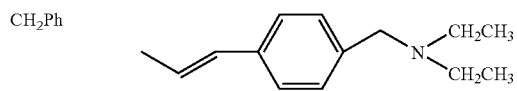 |
| 71 | CONH₂ | CH₂Ph | 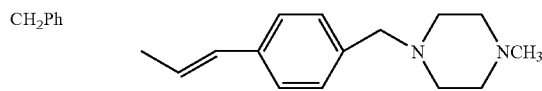 |
| 72 | H | CH₂Ph | 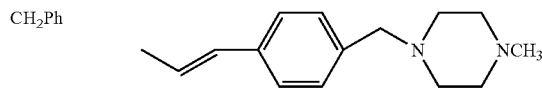 |
| 73 | CONH₂ | CH₂Ph | 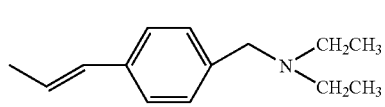 |
| 74 | H | (CH₂)₃CH₃ | 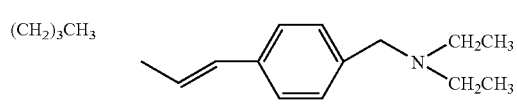 |
| 75 | CONH₂ | (CH₂)₃CH₃ | 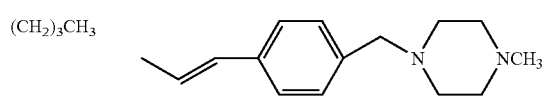 |
| 76 | H | (CH₂)₃CH₃ | 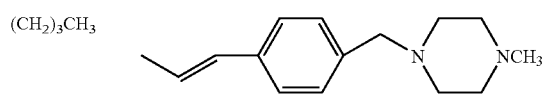 |
| 77 | CONH₂ | (CH₂)₃CH₃ | 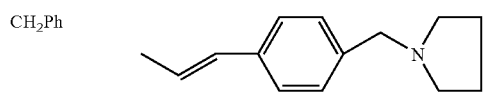 |
| 78 | H | CH₂Ph | 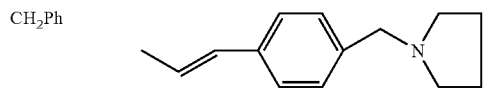 |
| 79 | CONH₂ | CH₂Ph | 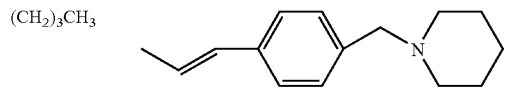 |
| 80 | H | (CH₂)₃CH₃ | 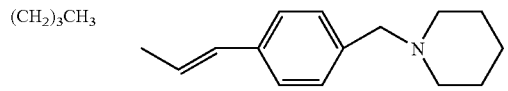 |
| 81 | CONH₂ | (CH₂)₃CH₃ | |

-continued
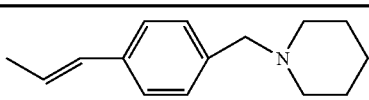
| Example | R' | R" | R''' |
|---|---|---|---|
| 82 | H | CH$_2$Ph | 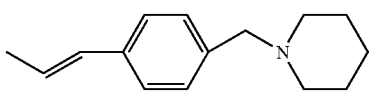 |
| 83 | CONH$_2$ | CH$_2$Ph | 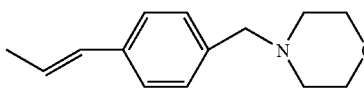 |
| 84 | H | CH$_2$Ph | 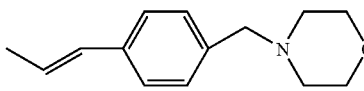 |
| 85 | CONH$_2$ | CH$_2$Ph | 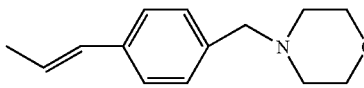 |
| 86 | H | (CH$_2$)$_3$Cl$_3$ | 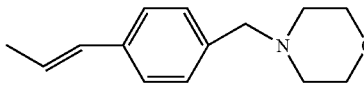 |
| 87 | CONH$_2$ | (CH$_2$)$_3$Cl$_3$ | 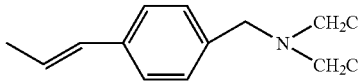 |
| 88 | H | CH$_2$Ph | 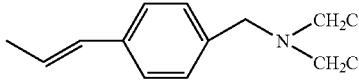 |
| 89 | CONH$_2$ | CH2Ph [sic] | 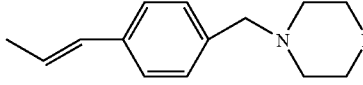 |
| 90 | H | CH2Ph [sic] | 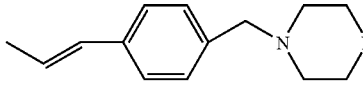 |
| 91 | CONH$_2$ | CH2Ph [sic] | 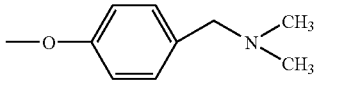 |
| 92 | H | CH$_2$Ph | 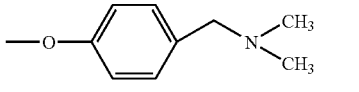 |
| 93 | CONH$_2$ | CH$_2$Ph | 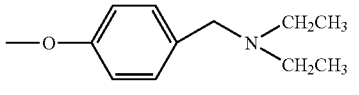 |
| 94 | H | CH$_2$Ph | 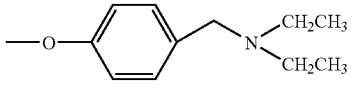 |
| 95 | CONH$_2$ | CH$_2$Ph | |

-continued

[Structure: 2-substituted benzamide with NH-CH(R")-C(=O)-R', ortho R''']

| Example | R' | R" | R''' |
|---------|-----|-----|------|
| 96 | H | CH₂Ph | 4-(4-methylpiperazin-1-ylmethyl)styryl |
| 97 | CONH₂ | CH₂Ph | 4-(4-methylpiperazin-1-ylmethyl)styryl |
| 98 | H | (CH₂)₃CH₃ | 4-(4-methylpiperazin-1-ylmethyl)styryl |
| 99 | CONH₂ | (CH₂)₃CH₃ | 4-(4-methylpiperazin-1-ylmethyl)styryl |

[Structure: nicotinamide (pyridine-3-CONH-) with CH(R")-C(=O)-R', R''' at 4-position]

| Example | R' | R" | R''' |
|---------|-----|-----|------|
| 100 | H | CH₂Ph | 4-(dimethylaminomethyl)styryl |
| 101 | CONH₂ | CH₂Ph | 4-(dimethylaminomethyl)styryl |
| 102 | H | (CH₂)₃CH₃ | 4-(dimethylaminomethyl)styryl |
| 103 | CONH₂ | (CH₂)₃CH₃ | 4-(dimethylaminomethyl)styryl |
| 104 | H | CH₂Ph | 4-(diethylaminomethyl)styryl |
| 105 | CONH₂ | CH₂Ph | 4-(diethylaminomethyl)styryl |
| 106 | H | | 4-(diethylaminomethyl)styryl |
| 107 | CONH₂ | (CH₂)₃CH₃ | 4-(diethylaminomethyl)styryl |

-continued

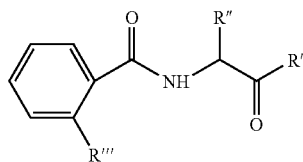

| Example | R' | R" | R''' |
|---|---|---|---|
| 108 | H | CH₂Ph | 4-(4-methylpiperazin-1-ylmethyl)styryl |
| 109 | CONH₂ | CH₂Ph | 4-(4-methylpiperazin-1-ylmethyl)styryl |
| 110 | H | (CH₂)₃CH₃ | 4-(4-methylpiperazin-1-ylmethyl)styryl |
| 111 | CONH₂ | (CH₂)₃CH₃ | 4-(4-methylpiperazin-1-ylmethyl)styryl |
| 112 | H | CH₂Ph | 4-(morpholin-4-ylmethyl)styryl |
| 113 | CONH₂ | CH₂Ph | 4-(morpholin-4-ylmethyl)styryl |
| 114 | H | (CH₂)₃Cl₃ | 4-(morpholin-4-ylmethyl)styryl |
| 115 | CONH₂ | (CE2)₃Cl₃ | 4-(morpholin-4-ylmethyl)styryl |
| 116 | H | CH₂Ph | 4-(pyrrolidin-1-ylmethyl)styryl |
| 117 | CONH₂ | CH₂Ph | 4-(pyrrolidin-1-ylmethyl)styryl |
| 118 | H | (CH₂)₃Cl₃ | 4-(pyrrolidin-1-ylmethyl)styryl |
| 119 | H | (CH₂)₃Cl₃ | 4-(pyrrolidin-1-ylmethyl)styryl |
| 120 | H | (CH₂)₃Cl₃ | 4-(piperidin-1-ylmethyl)styryl |
| 121 | CONH₂ | (CH₂)₃Cl₃ | 4-(piperidin-1-ylmethyl)styryl |

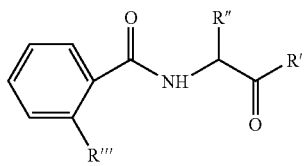

| Example | R' | R" | R''' |
|---|---|---|---|
| 122 | H | CH$_2$Ph | (E)-4-(piperidin-1-ylmethyl)styryl group |
| 123 | CONH$_2$ | CH$_2$Ph | (E)-4-(piperidin-1-ylmethyl)styryl group |

Example 44

N-(1-Carbamoyl-1-oxo-hexan-2-yl)-2-(E-2-(4-(piperidin-1-yl-methyl)-phenyl)-ethen-1-yl)-benzamide Ms: m/e=462 (M++1).

Example 60

N-(1-Carbamoyl-1-oxo-3-phenyl-propan-2-yl)-2-(E-2-(4-(4-ethylpiperazin-1-ylmethyl)-phenyl)-ethen-1-yl)-benzamide Ms: m/e=524 (M+).

Example 66

N-(1-Carbamoyl-1-oxo-3-phenyl-propan-2-yl)-2-(E-2-(4-(4-phenylpiperazin-1-ylmethyl)-phenyl)-ethen-1-yl)-benzamide $^1$H-NMR (D$_6$-DMSO): δ=2.4 (1H), 2.5 (4H), 2.9 (1H), 3.1 (4H), 3.3 (1H), 3.6 (2H), 5.4 (1H), 6.8 (1H), 6.9 (2H) and 7.1-8.0 (18H) ppm.

Example 71

N-(1-Carbamoyl-1-oxo-3-phenyl-propan-2-yl)-2-(E-2-(4-(N,N-diethylaminomethyl)-phenyl)-ethen-1-yl)-nicotinamide $^1$H-NMR (D$_6$-DMSO): δ=1.0 (6H), 2.85 (1H), 3.3 (1H), 3.6 (4H), 5.4 (1H), 7.2-8.0 (11H), 8.6 (1H) and 9.2 (1H) ppm.

Example 75

N-(1-Carbamoyl-1-oxo-hexan-2-yl)-2-(E-2-(4-(N,N-diethylaminomethyl)-phenyl)-ethen-1-yl)-nicotinamide $^1$H-NMR (D$_6$-DMSO): δ=1.0 (9H), 2.5 (4H), 3.5 (2H), 5.2 (1H), 7.3-8.2 (12H), 8.7 (1H) and 9.0 (1H) ppm.

Example 77

N-(1-Carbamoyl-1-oxo-hexan-2-yl) -2-(E-2-(4-(4-methylpiperazin-1-ylmethyl)-phenyl)-ethen-1-yl)-benzamide $^1$H-NMR (D$_6$-DMSO): δ=0.9-1.9 (9H), 2.8 (4H), 5.2 (1H), 7.3-8.0 (12H), 8.1 (1H) and 8.8 (1H) ppm.

Example 79

N-(1-Carbamoyl-1-oxo-3-phenyl-propan-2-yl)-2-(E-2-(4-(pyrrolidin-1-ylmethyl)-phenyl)-ethen-1-yl)-nicotinamide $^1$H-NMR (CF$_3$ COOD): δ=2.1-2.4 (2H), 3.1-3.4 (3H), 3.6-3.9 (3H), 4.4 (2H), 5.2 (1H), 7.0-8.0 (16H) and 8.8 (1H) ppm.

Example 81

N-(1-Carbamoyl-1-oxo-hexan-2-yl)-2-(E-2-(4-(piperidin-1-ylmethyl)-phenyl)-ethen-1-yl)-nicotinamide $^1$H-NMR (D$_6$-DMSO): δ=0.9-1.9 (15H), 2.9 (2H), 3.2 (2H), 4.3 (2H), 5.2 (2H), 7.5-8.1 (11H), 8.8 (1H) and 9.0 (1H) ppm.

Example 83

N-(1-Carbamoyl-1-oxo-3-phenyl-propan-2-yl)-2-(E-2-(4-(piperidin-1-ylmethyl)-phenyl)-ethen-1-yl)-nicotinamide $^1$H-NMR (CF$_3$ COOD): δ=1.6-2.2 (6H); 3.0-3.2 (3H), 3.6-3.8 (2H), 4.3 (2H), 6.1 (1H), 7.0-8.0 (14H) and 8.8 (1H) ppm.

Example 85

N-(1-Carbamoyl-1-oxo-3-phenyl-propan-2-yl)-2-(E-2-(4-(morpholin-1-ylmethyl)-phenyl)-ethen-1-yl)-nicotinamide $^1$H-NMR (D$_6$-DMSO): δ=2.35 (2H), 2.8 (1H), 3.3 (1H), 3.5 (2H), 3.6 (2H), 5.4 (1H), 7.0-8.0 (14H), 8.1 (1H), 8.6 (1H) and 9.2 (1H) ppm.

Example 124

N-(1-Carbamoyl-1-oxo-3-phenyl-propan-2-yl)-2-(E-2-(4-(N,N-diethylaminomethyl)-phenyl)-ethen-1-yl)-nicotinamide x dihydrochloride $^1$H-NMR (D$_6$-DMSO): δ=1.1 (6H), 2.9 (1H), 3.1 (4H), 3.3 (1H), 4.3 (2H), 5.5 (1H), 7.2-8.0 (13H), 8.7 (2H), 9.3 (1H) and 10.8 broad) ppm.

Example 125

N-(1-Carbamoyl-1-oxo-3-phenyl-propan-2-yl)-2-(E-2-(4-(N,N-dimethylaminomethyl)-phenyl)-ethen-1-yl)-nicotinamide x dihydrochloride $^1$H-NMR (D$_6$-DMSO): δ=2.7 (6H), 2.9 (1H), 3.2 (1H), 4.3 (2H), 5.5 (1H), 7.2-8.0 (16H) and 8.6 (1H) ppm.

Example 126

N-(Butan-1-al-2-yl)-2-(E-2-(4-(N,N-dimethylaminomethyl)phenyl)-ethen-1-yl)-5-methoxybenzamide $^1$H-NMR (CDCL$_3$) [sic]: δ=1.0 (3H), 1.8 (1H), 2.1 (1H), 3.0 (6H), 3.8 (3H), 4.6 (2H), 4.8 (1H), 6.4 (1H), 6.8-7.2 (3H), 7.3-7.8 (6H) and 9.7 (1H) ppm.

Example 127

2-(E-2-(4-(N,N-Dimethylaminomethyl)phenyl)-ethen-1-yl)-5-methoxy-N-(pentan-1-al-2-1)-benzamide [sic]

Example 128

N-(3-Cyclohexyl-propan-al-2-yl)-2-(E-2-(4-(piperidin-1-yl-methyl)phenyl)-ethen-1-yl)-benzamide [sic]

$^1$H-NMR (CDCL$_3$) [sic]: δ=1.0 (2H), 1.2 (3H), 1.5 (4H), 1.7 (8H), 1.8 (2H), 2.5 (3H), 3.6 (2H), 4.9 (1H), 6.2 (1H), 7.1 (1H), 7.3 (1H), 7.4 (2H), 7.5 (5H), 7.7 (1H) and 9.6 (1H) ppm.

Example 129

N-(4-Methylpentan-1-al-2-yl)-2-(E-2-(4-(piperidin-1-yl-methyl)phenyl)-ethen-1-yl)-benzamide [sic]

$^1$H-NMR (CDCL$_3$) [sic]: δ=0.9 (3H), 1.0 (3H), 1.4 (3H), 1.6 (6H), 1.8 (2H), 2.4 (2H), 3.5 (2H), 4.8 (1H), 6.2 (1H), 7.0 (1H), 7.2-7.6 (8H), 7.7 (1H) and 9.7 (1H) ppm.

Example 130

N-(Pentan-1-al-2-yl)-2 (E-2-(4-(piperidin-1-yl-methyl)phenyl)-ethen-1-yl)-benzamide [sic]

$^1$H-NMR (CDCL$_3$) [sic]: δ=0.9 (3H), 1.4-1.6 (10H), 2.4 (4H), 3.4 (2H), 4.8 (1H), 6.3 (1H), 7.0 (1H), 7.2-7.6 (7H), 7.7 (1H) and 9.7 (1H) ppm.

Example 131

2-(E-2-(4-(N,N-Dimethylamino-methyl)phenyl)-ethen-1-yl)-N-(3-phenyl-propan-1-al-2-yl)-5-methoxy-benzamide [sic]

$^1$H-NMR (CDCL$_3$) [sic]: δ=2.3 (6H), 3.3 (2H), 3.6 (2H), 3.8 (3H), 4.9 (1H), 6.5 (1H), 7.0-7.4 (13H), 8.5 (1H) and 9.7 (1H) ppm.

Example 132

N-(3-(3-Indolyl)-propan-1-al-2-yl)-2-(E-2-(4-(piperidin-1-yl-methyl)phenyl)-ethen-1-yl)-benzamide [sic]

$^1$H-NMR (CDCL$_3$) [sic]: δ=1.4 (2H), 1.6 (4H), 2.4 (4H), 3.4 (2H), 3.5 (2H), 5.1 (1H), 6.4 (1H), 6.9 (2H), 7.1-7.5 (11H), 7.6 (2H), 8.1 (1H) and 9.8 (1H) ppm.

Example 133

N-(3-(4-Imidazolyl)-propan-1-al-2-yl)-2-(E-2-(4-(piperidin-1-yl-methyl)phenyl)-ethen-1-yl)-benzamide [sic]

$^1$H-NMR (D$_6$-DMSO): δ=1.4 (2H), 1.6 (4H), 2.4 (4H), 3.4 (2H), 4.1 (2H), 4.6 (1H), 7.1 (1H), 7.2-7.7 (11H), 7.8 (1H), 8.9 (1H) and 9.7 (1H) ppm.

Example 134

N-(3-Cyclohexyl-propan-1-al-2-yl)-2-(E-2-(4-(morpholin-1-yl-methyl)phenyl)-ethen-1-yl)-benzamide [sic]

$^1$H-NMR (CDCl$_3$): δ=0.8-1.7 (11H), 1.8 (2H), 2.8 (4H), 3.8 (6H), 4.9 (1H), 6.4 (1H), 7.0 (1H); 7.2-7.6 (8H), 7.7 (1H) and 9.6 (1H) ppm.

Example 135

N-(4-Methyl-pentan-1-al-2-yl)-2-(E-2-(4-(morpholin-1-yl-methyl)phenyl)-ethen-1-yl)-benzamide [sic]

$^1$H-NMR (CDCl$_3$) [sic]: δ=1.0 (6H), 1.5 (2H), 2.1 (1H), 2.8 (4H), 3.7-3.9 (6H), 4.8 (1H), 6.3 (1H), 7.0 (1H), 7.2-7.8 (9H) and 9.7 (1H) ppm.

Example 136

2-(E-2-(4-(Morpholin-1-yl-methyl)phenyl)-ethen-1-yl)-N-(pentan-1-al-2-yl)-benzamide $^1$H-NMR (CDCl$_3$) [sic]: δ=1.0 (3H), 1.5 (2H), 1.7 (2H), 2.4 (4H), 3.4 (2H), 3.7 (4H), 4.9 (1H), 6.3 (1H), 7.0 (1H), 7.2-7.6 (8H), 7.7 (1H) and 9.7 (1H) ppm.

Example 137

N-(1-Carbamoyl-1-oxo-3-phenyl-propan-2-yl)-2-(E-2-(4-(pyrrolidon-1-yl-methyl)-phenyl)-ethen-1-yl)-benzamide x methanesulfonic acid $^1$H-NMR (D$_6$-DMSO): δ=1.8-2.1 (2H), 2.3 (3H), 2.6-2.9 (2H), 3.1-3.3 (2H), 4.25 (2H), 4.8 (1H), 7.0-8.0 (17H) and 9.8 (1H) ppm.

Example 138

N-(1-Carbamoyl-1-oxo-3-phenyl-propan-2-yl)-2-(E-2-(4-(morpholin-1-yl-methyl)-phenyl)-ethen-1-yl)-benzamide x methanesulfonic acid $^1$H-NMR (D$_6$-DMSO): δ=2.3 (3H), 2.8 (1H), 3.2 (1H), 3.7 (2H), 3.9 (2H), 4.2 (1H), 5.3 (1H), 7.0-7.7 (14H), 7.9 (2H), 8.1 (1H), 9.0 (1H) and 9.8 broad) ppm.

Example 139

N-(3-Imidazolyl-propan-1-al-2-yl)-2-(E-2-(4-(morpholin-1-yl-methyl)phenyl)-ethen-1-yl)-benzamide [sic]

$^1$H-NMR CDCl$_3$): δ=2.4-2.8 (6H), 3.5 (2H), 3.7 (4H), 4.8 (1H), 6.6-7.6 (13H), 7.9 (1H) and 9.6 (1H) ppm.

Example 140

N-(3-Indolyl-propan-1-al-2-yl)-2-(E-2-(4-(morpholin-1-yl-methyl)phenyl)-ethen-1-yl)-benzamide [sic]

$^1$H-NMR (D$_6$-DMSO): δ=2.4 (6H), 3.4 (4H), 3.6 (4H), 4.7 (1H), 6.9-7.9 (16H), 8.1 (1H) and 9.7 (1H) ppm.

Example 141

2-(E-2-(4-(N,N-Dimethylamino-methyl)phenyl)-ethen-1-yl)-N-(3-indolyl-propan-1-al-2-yl)-benzamide [sic]

$^1$H-NMR (CDCL$_3$) [sic]: δ=2.3 (6H), 3.4 (4H), 5.1 (1H), 6.4 (1H), 6.9 (1H), 7.0-7.5 (13H), 7.6 (2H) and 9.6 (1H) ppm.

Example 142

N-(1-Carbamoyl-1-oxo-propan-2-yl)-2-(E-2-(4-(N,N-dimethylamino-methyl)-phenyl)-ethen-1-yl)-benzamide hydrochloride $^1$H-NMR (D$_6$-DMSO): δ=1.3 (3H), 2.7 (6H), 4.3 (2H), 5.1 (1H), 7.3-8.0 (11H), 8.1 (1H), 9.0 (1H) and 11.2 (broad) ppm.

Example 143

N-(1-Carbamoyl-1-oxo-propan-2-yl)-2-(E-2-(4-(morpholin-1-yl-methyl)-phenyl)-ethen-1-yl)-nicotinamide dihydrochloride $^1$H-NMR (D$_6$-DMSO): δ=1.4 (3H), 3.1 (2H), 3.2 (2H), 3.8-4.0 (4H), 4.4 (2H), 5.2 (1H), 7.5-8.2 (10H), 8.7 (1H), 9.2 (1H) and 11.6 broad) ppm.

Example 144

N-(1-Carbamoyl-1-oxo-propan-2-yl)-2-(E-2-(4-(morpholin-1-yl-methyl)-phenyl)-ethen-1-yl)-benzamide hydrochloride $^1$H-NMR (D$_6$-DMSO): δ=1.3 (3H), 3.1 (2H), 3.2 (2H), 3.8 (2H), 3.9 (2H), 4.3 (2H), 5.1 (1H), 7.3-8.0 (11H), 8.1 (1H), 8.9 (1H) and 11.4 (broad) ppm.

Example 145

N-(1-Carbamoyl-1-oxo-propan-2-yl)-2-(E-2-(4-(4-methylpiperazin-1-yl-methyl)-phenyl)-ethen-1-yl)-benzamide dihydrochloride $^1$H-NMR (D$_6$-DMSO): δ=1.35 (3H), 3.0-3.3 (4H), 3.8-4.0 (4H), 4.3 (2H), 5.1 (1H), 7.3-8.1 (12H), 8.9 (1H) and 11.5 (broad) ppm.

Example 146

N-(1-Carbamoyl-1-oxo-hexan-2-yl)-2-(E-2-(4-(4-methylpiperidin-1-yl-methyl)-phenyl)-ethen-1-yl)-benzamide

Example 147

N-(1-Carbamoyl-1-oxo-3-phenyl-propan-2-yl)-2-(E-2-(4-(4-methyl-piperidin-1-yl-methyl)-phenyl)-ethen-1-yl)-benzamide

Example 148

N-(1-Carbamoyl-1-oxo-3-phenyl-propan-2-yl)-2-(E-2-(4-(N-(n-propyl)-N-(2-methyl-propan-1-yl)aminomethyl)-phenyl)-ethen-1-yl)-benzamide $^1$H-NMR (CDCL$_3$) [sic]: δ=0.9 (9H), 1.4 (2H), 1.8 (1H), 2.2 (2H), 2.3 (2H), 3.2-3.6 (4H), 5.6 (1H), 5.9 (1H), 6.4 (1H) and 6.8-7.8 (16H) ppm.

Example 149

N-(1-Carbamoyl-1-oxo-hexan-2-yl)-2-(E-2-(4-(N-(isopropyl)-N-(n-propyl)aminomethyl)-phenyl)-ethen-1-yl)-benzamide $^1$H-NMR (CDCL$_3$) [sic]: δ=0.8 (6H), 1.0 (6H), 1.2-1.4 (4H), 1.7 (1H), 2.0 (1H), 2.4 (3H), 3.0 (1H), 3.0-3.2 (1H), 3.6 (2H), 5.4 (1H), 5.8 (1H), 6.4 (1H), 6.8 (1H), 7.0 (1H), 7.2-7.4 (7H), 7.6 (1H) and 7.7 (1H) ppm.

Example 150

N-(1-Carbamoyl-1-oxo-hexan-2-yl)-2-(E-2-(4-(N-(n-propyl)-N-(2-methyl-propan-1-yl)aminomethyl)-phenyl)-ethen-1-yl)-benzamide $^1$H-NMR (CDCL$_3$) [sic]: δ 0.9 (12H), 1.2-1.5 (5H), 1.7 (2H), 2.1 (2H), 2.4 (4H), 3.5 (2H), 5.4 (1H), 5.8 (1H), 6.4 (1H), 6.8 (1H), 7.0 (1H) and 7.2-7.6 (9H) ppm.

Example 151

N-(1-Carbamoyl-1-oxo-3-phenyl-propan-2-yl)-2-(E-2-(4-(N-(isopropyl)-N-(n-propyl)aminomethyl)-phenyl)-ethen-1-yl)-benzamide $^1$H-NMR (CDCl$_3$): δ 0.8 (3H), 1.2 (6H), 1.5 (2H), 2.4 (2H), 2.9-3.4 (3H), 3.6 (2H), 4.6 (1H), 5.8 (1H), 6.4 (1H) and 6.8-7.8 (16H) ppm.

Example 152

N-(1-Carbamoyl-1-oxo-3-phenyl-propan-2-yl)-2-(E-2-(4-((3,5dimethylmorpholin-1-yl)methyl)-phenyl)-ethen-1-yl)-benzamide $^1$H-NMR (D$_6$-DMSO): δ 1.0 (6H), 1.7 (2H), 2.8-3.7 (8H), 5.5 (1H), 7.1-7.8 (15H), 8.1 (1H) and 9.0 (1H) ppm.

Example 153

N-(1-Carbamoyl-1-oxo-3-phenyl-propan-2-yl)-2-(E-2-(4-(N,N-(dimethoxyeth-1-yl)aminomethyl)-phenyl)-ethen-1-yl)-benzamide hydrochloride $^1$H-NMR (D$_6$-DMSO): δ 3.3-3.8 (10H), 4.5 (2H), 5.5 (1H), 7.0-8.0 (17H) and 9.0 (1H) ppm.

Example 154

2-(E-2-(4-(4-tert-Butyl-piperidin-1-yl-methyl)-phenyl)-ethen-1-yl)-N-(1-carbamoyl-1-oxo-3-phenyl-propan-2-yl)-benzamide $^1$H-NMR (CDCl$_3$): δ 0.9 (9H), 1.1 (1H), 1.6 (4H), 2.2 (2H), 3.2 (4H), 3.8 (2H), 5.6 (1H), 5.8 (1H), 5.9 (1H), 6.4 (1H), 6.9-7.6 (14H) and 7.7 (1H) ppm.

Example 155

2-(E-2-(4-(4-tert-Butyl-piperidin-1-yl-methyl)-phenyl)-N-(1-carbamoyl-1-oxo-hexan-2-yl)ethen-1-yl)benzamide $^1$H-NMR (CDCl$_3$): δ 0.9 (9H), 1.2-2.0 (9H), 2.5 (2H), 2.8 (2H), 3.2 (2H), 3.3 (1H), 3.5 (2H), 4.1 (2H), 5.4 (1H), 5.9 (1H), 6.4 (1H), 7.0 (1H), 7.2 (2H), 7.4-7.6 (7H) and 7.7 (1H) ppm.

Example 156

2-(E-2-(4-N,N-n-Butyl-methylaminomethyl)-phenyl)-ethen-1-yl)-N-(1-carbamoyl-1-oxo-hexan-2-yl)-benzamide [sic]

$^1$H-NMR (D$_6$-DMSO): δ 0.7 (6H), 1.2 (6H), 1.4 (2H), 2.3 (6H), 2.5 (3H), 2.7 (4H), 4.0 (2H), 4.9 (1H), 5.8 (1H), 6.9-7.4 (8H), 7.7 (2H) and 8.7 (1H) ppm.

Example 157

2-(E-2-(4-N,N-n-Butyl-methylaminomethyl)-phenyl)-ethen-1-yl)-N-(1-carbamoyl-1-oxo-3-phenyl-propan-2-yl)-benzamide [sic]

Example 158

N-(1-Carbamoyl-1-oxo-3-phenyl-propan-2-yl)-(E-2 (4-(N,N-n-propyl-methylaminomethyl)-phenyl)-ethen-1-yl)-benzamide [sic]

Example 159

N-(1-Carbamoyl-1-oxo-3-phenyl-propan-2-yl)-2-(E-2(4-(N,N-(2-methyl-but-2-yl)-methylaminomethyl-phenyl)-ethen-1-yl)-benzamide [sic]

Example 160

N-(1-Carbamoyl-1-oxo-hexan-2-yl)-2-(E-2-(4-(N,N-(2-methyl-but-2-yl)-methylaminomethyl)-phenyl)-ethen-1yl)-benzamide [sic]

Example 161

N-(1-Carbamoyl-1-oxo-hexan-2-yl)-2-(E-2-(4-(N,N-n-propyl-methylaminomethyl)-phenyl)-ethen-1-yl)-benzamide [sic]

$^1$H-NMR (D$_6$-DMSO): δ 0.8 (6H), 1.3 (4H), 1.7 (2H), 2.4-2.6 (5H), 2.8 (2H), 4.0-4.2 (2H), 5.1 (1H), 7.1-7.6 (9H), 7.8 (2H), 8.1 (1H) and 8.8 (1H) ppm.

Example 162

2-(E-2-(4-(N,N-n-Butyl-ethylaminomethyl)-phenyl)-ethen-1-yl)-N-(1-carbamoyl-1-oxo-3-phenyl-propan-2-yl)-benzamide [sic]

Example 163

N-(1-Carbamoyl-1-oxo-3-phenyl-propan-2-yl)-2-(E-2-(4-(hexahydroazepin-1-yl-methyl)-phenyl)-ethen-1-yl)-benzamide

Example 164

N-(1-Carbamoyl-1-oxo-n-hexan-2-yl)-2-(E-2-(4-(hexahydroazepin-1-yl-methyl-phenyl)-ethen-1-yl)-benzamide

Example 165

N-(1-Carbamoyl-1-oxo-3-phenyl-propan-2-yl)-2-(E-2-(4-(N,N-diethylaminomethyl)-phenyl)-ethen-1-yl)-benzamide x methanesulfonic acid $^1$H-NMR (D$_6$-DMSO): δ 1.2 (6H), 2.3 (3H), 2.9 (1H), 3.1 (4H), 3.2 (1H), 4.3 (2H), 5.4 (1H), 7.2-8.0 (15H), 8.2 (1H), 8.9 (1H) and 9.4 (1H) ppm.

Example 166

2-(E-2-(4-(N,N-n-Butyl-ethylaminomethyl)-phenyl)-ethen-1-yl)-N-(1-carbamoyl-1-oxo-n-hexan-2-yl)-benzamide [sic]

$^1$H-NMR (D$_6$-DMSO): δ 0.8 (6H), 1.2-1.5 (7H), 1.5-1.8 (4H), 2.6 (2H), 2.9 (2H), 3.0 (2H), 4.3 (2H), 5.2 (1H), 7.2-7.7 (9H), 7.8 (2H), 8.1 (1H) and 8.9 (1H) ppm.

Example 167

N-(1-Carbamoyl-1-oxo-3-phenyl-propan-2-yl)-2-(E-2-(4-(N,N-diethylaminomethyl)-phenyl)-ethen-1yl)-4-methyl-benzamide hydrochloride MS: m/e=469 (M+)

Example 168

N-(1-Carbamoyl-1-oxo-n-hexan-2-yl)-2-(E-2-(4-(N-ethyl-N-isopropylaminomethyl)-phenyl)-ethen-1-yl)-benzamide ¹H-NMR (CDCl₃): δ 0.5 (9H), 1.0 (3H), 1.3 (3H), 1.8 (2H), 2.1 (2H), 2.4 (4H), 3.5 (2H), 5.4 (1H), 5.7 (1H), 6.4 (1H), 6.8 (1H), 7.1 (1H), 7.2-7.6 (8H) and 7.7 (1H) ppm.

Example 169

N-(1-Carbamoyl-1-oxo-3-phenyl-propan-2-yl)-2-(E-2-(4-(N-ethyl-N-isopropylaminomethyl)-phenyl)-ethen-1-yl)-benzamide ¹H-NMR (CDCl₃): δ 0.9 (6H), 1.0 (3H), 1.8 (1H), 2.2 (2H), 2.4 (2H), 3.1 (2H), 3.6 (2H), 5.7 (1H), 6.4 (1H), 6.9-7.5 (16H) and 7.7 (1H) ppm.

Example 170

N-(1-Carbamoyl-1-oxo-n-hexan-2-yl)-2-(E-2-(4-(N-cyclohexyl-N-methylaminomethyl)-phenyl)-ethen-1-yl)-benzamide ¹H-NMR (CDCl₃): d 0.8 (3H), 1.1-1.5 (9H), 1.6-2.1 (6H), 2.2 (3H), 2.5 (2H), 3.6 (2H), 5.4 (1H), 5.8 (1H), 6.4 (1H), 6.8 (1H), 7.0 (1H), 7.2-7.6 (8H) and 7.8 (1H) ppm.

Example 171

N-(1-Carbamoyl-1-oxo-n-hexan-2-yl)-2-(E-2-(4-(N-methylpiperazin-1-yl-methyl)-phenyl)-ethen-1-yl)-nicotinamide dihydrochloride ¹H-NMR (D₆DMSO): δ 0.9-1.9 (10H), 2.8 (2H), 4.4 (2H), 5.2 (1H), 7.4-8.2 (13H), 8.7 (1H) and 9.1 (1H) ppm.

Example 172

N-(1-Carbamoyl-1-oxo-3-phenyl-propan-2-yl)-2-(E-2-(4-(methyl-piperazin-1-yl-methyl)-phenyl)-ethen-1-yl)-nicotinamide dihydrochloride MS: m/e=511 (M+)

Example 173

N-(1-Carbamoyl-1-oxo-3-phenyl-propan-2-yl)-2-(E-2-(4-(N-cyclohexyl-N-methylaminomethyl)-phenyl)-ethen-1-yl)-benzamide ¹H-NMR (CDCl₃): δ 0.9 (2H), 1.1-1.4 (7H), 1.6 (1H), 1.8 (2H), 2.1 (2H), 2.4 (3H), 3.9 (2H), 5.5 (1H), 5.9 (1H), 6.4 (1H) and 6.8-7.8 (16H) ppm.

Example 174

N-(1-Carbamoyl-1-oxo-3-phenyl-propan-2-yl)-2-(E-2-(4-(morpholin-1-yl-methyl)-phenyl)-ethen-1-yl)-nicotinamide dihydrochloride ¹H-NMR (D₆DMSO): δ 2.8 (1H), 3.0-3.4 (5H), 3.8-4.0 (4H), 4.4 (2H), 5.5 (1H), 7.0-8.0 (13H), 8.2 (1H), 8.7 (1H), 8.7 (1H), 9.2 (1H) and 11.8 (broad) ppm.

Example 175

N-(1-Carbamoyl-1-oxo-3-phenyl-propan-2-yl)-2-(E-2-(4-(N,N-dimethylamino-methyl)-phenyl-ethen-1-yl)-nicotinamide dihydrochloride ¹H-NMR (D₆DMSO): δ 1.3 (6H), 2.9 (1H), 3.0-3.2 (4H), 3.3 (1H), 4.3 (2H), 5.4 (1H), 7.2-8.0 (13H), 8.2 (1H), 8.7 (1H), 9.2 (1H) and 10.6 (broad) ppm.

Example 176

N-(1-Carbamoyl-1-oxo-3-phenyl-propan-2-yl)-2-(E-2-(4-(1,2,5,6-tetrahydropyridin-1-yl-methyl)-phenyl)-ethen-1-yl)-benzamide MS: m/e=493 (M+)

Example 177

N-(1-Carbamoyl-1-oxo-3-phenyl-propan-2-yl)-3-chloro-2-(E-2-(4-(N,N-dimethylamino-methyl)-phenyl)-ethen-1-yl)-benzamide

Example 178

N-(1-Carbamoyl-1-oxo-3-phenyl-propan-2-yl)-2-(E-2-(4-(4-methyl-piperazin-1-yl-methyl)-phenyl)-ethen-1-yl)-benzamide x 2 methanesulfonic acid ¹H-NMR (D₆-DMSO): δ 2.4 (12H), 2.8-3.7 (11H), 4.5 (2H), 5.4 (1H), 7.2-8.0 (18H), 8.2 (1H) and 9.0 (1H) ppm.

Example 179

N-(1-Carbamoyl-1-oxo-n-butan-2-yl)-2-(E-2-(4-(morpholin-1-yl-methyl)-phenyl)-ethen-1-yl-benzamide hydrochloride ¹H-NMR (D₆-DMSO): δ 1.0 (3H), 1.6 (1H), 1.9 (1H), 3.0-3.4 (4H), 3.7-4.0 (4H), 4.3 (2H), 5.2 (1H), 7.2-8.2 (12H), 8.9 (1H) and 11.8 (broad) ppm.

Example 180

N-(1-Carbamoyl-3-methyl-1-oxo-n-butan-2-yl) -2-(E-2-(4-(4-methyl-piperazin-1-yl-methyl)-phenyl)-ethen-1-yl-benzamide x 2 methanesulfonic acid ¹H-NMR (D₆-DMSO): δ0.9-1.1 (6H), 2.3 (3H), 2.8 (3H), 3.0-3.8 (8H), 3.9 (2H), 5.1 (1H), 7.0-8.1 (12H) and 8.8 (1H) ppm.

Example 181

N-(1-Carbamoyl-3-methyl-1-oxo-n-butan-2-yl)-2-(E-2-(4-(morpholin-1-yl-methyl)-phenyl)-ethen-1-yl)-benzamide x methanesulfonic acid ¹H-NMR (D₆-DMSO): δ 0.9-1.1 (6H), 2.3 (4H), 3.0-3.5 (4H), 3.6-4.0 (4H), 4.4 (2H), 5.2 (1H), 7.2-8.1 (12H), 8.8 (1H) and 9.8 (broad) ppm.

Example 182

N-(1-Carbamoyl-1-oxo-n-butan-2-yl)-2-(E-2-(4-(4-methylpiperazin-1-yl-methyl)-phenyl)-ethen-1-yl-benzamide dihydrochloride $^1$H-NMR (D$_6$-DMSO): δ 1.0 (3H), 1.6 (1H), 1.9 (1H), 2.8 (3H), 3.3-3.8 (10H), 5.1 (1H), 7.3-8.1 (12H), and 8.8 (1H) ppm.

Example 183

N-(1-Carbamoyl-1-oxo-n-hexan-2-(4-(piperidin-1-yl-methyl)-phenyl)-benzamide [sic]

Example 184

N-(1-Carbamoyl-1-oxo-3-phenyl-propan-2-yl)-2-(4-(piperidin-1-yl-methyl)-phenyl)-benzamide

Example 185

N-(1-Carbamoyl-1-oxo-3-phenyl-propan-2-yl)-2-(N-methyl-tetrahydroisoquinolin-7-yl)oxy-nicotinamide Ms: m/e=458 (M+)

Example 186

N-(1-Carbamoyl-1-oxo-3-phenyl-propan-2-yl)-2-(N-methyl-tetrahydroisoquinolin-7-yl)oxy-benzamide Ms: m/e=458 (M+)

Example 187

N-(3-Phenyl-propan-1-al-2-yl)-2-(4-(piperidin-1-yl-methyl)-benzyloxy)-nicotinamide [sic]

Example 188

2-(4-(N,N-Dimethylaminomethyl)-benzyloxy)-N-(3-phenyl-propan-1-al-2-yl)nicotinamide [sic]

Example 189

N-(3-Phenyl-propan-1-al-2-yl)-2-(4-(4-methylpiperazin-1-yl-methyl)-benzyloxy)-nicotinamide

Example 190

N-(1-Carbamoyl-1-oxo-3-phenyl-propan-$^2$-yl)-2-(4-(2-(N,N,dimethylamino)-eth-1-yl))-phenyloxy-nicotinamide hxydrochloride [sic]

What is claimed is:

1. An amide of the formula I

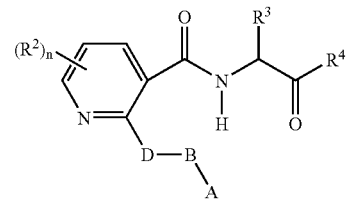

and its tautomeric forms, enantiomeric and diastereomeric forms, E and Z forms, and possible physiologically tolerated salts, in which the variables have the following meanings:

A is —(CH$_2$)p—R$^1$, where R$^1$ is selected from the group consisting of pyrrolidine, morpholine, hexahydroazepine piperidine, —NR$^5$R$^6$ and

wherein the cyclic amines are optionally substituted by one or two R$^{15}$ radicals, and R$^{15}$ is selected from the group consisting of hydrogen, C$_1$-C$_6$-alkyl, O—C$_1$-C$_6$-alkyl or phenyl, and R$^5$, R$^6$ and R$^7$ are, independently of one another, selected from the group consisting of hydrogen, C$_1$-C$_4$-alkyl, cyclohexyl, cyclopentyl, CH$_2$Ph, Ph and CH$_2$CH$_2$Ph, wherein the phenyl rings are optionally substituted by R$^6$, and P is 1 or 2, and B is phenyl, which is optionally substituted by up to two R$^8$ radicals, and A and B together can also be

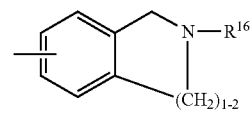

and

R$^{16}$ is selected from the group consisting of hydrogen, C$_1$-C$_6$-alkyl or (CH$_2$)$_{1-4}$-phenyl, wherein the phenyl ring is optionally substituted by up to two R$^6$ radicals, and D is selected from the group consisting of a bond, —(CH$_2$)$_{0-2}$—O—(CH$_2$)$_{0-2}$, —(CH$_2$)$_m$—, —CH=CH—, and —C≡C—, and R$^2$ is selected from the group consisting of chlorine, bromine, fluorine, C$_1$-C$_6$-alkyl, NHCO—C$_1$-C$_4$-alkyl, NHSO$_2$—C$_1$-C$_4$-alkyl, NO$_2$, —O—C$_1$-C$_4$-alkyl or NH$_2$, R$^3$ is C$_1$-C$_6$-alkyl, branched or unbranched, and which may also carry a SCH$_3$ radical, a phenyl ring, imidazolyl ring, indolyl ring or a cyclopentyl, cycloheptyl or cyclohexyl ring which is in turn substituted by up to of two R$^8$ radicals, where R$^8$ is selected from the group consisting of hydrogen, C$_1$-C$_4$-alkyl, branched or unbranched, —O—C$_1$-C$_4$-alkyl, OH, Cl, F, Br, I, CF$_3$, NO$_2$, NH$_2$, ON, COOH, COO—C$_1$-C$_4$-alkyl, NHCO—C$_1$-C$_4$-alkyl, —NHSO$_2$—C$_1$-C$_4$-alkyl and —SO$_2$—C$_1$-C$_4$-alkyl; and R$^4$ is selected from the group consisting of hydrogen, COOR$^9$, CO—Z in which Z is NR$^{10}$R$^{11}$

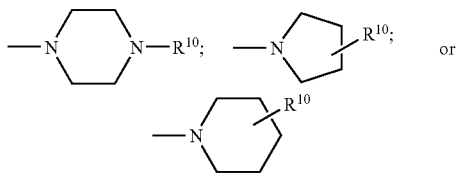

R$^9$ is hydrogen or C$_1$-C$_6$-alkyl, linear or branched, which may be substituted by a phenyl ring which may itself also be substituted by one or two R$^{12}$ radicals, and R$^{10}$ is hydrogen or C$_1$-C$_6$-alkyl, linear or branched, which may be substituted by a phenyl ring which itself may also be substituted by one or two R$^{12}$ radicals,

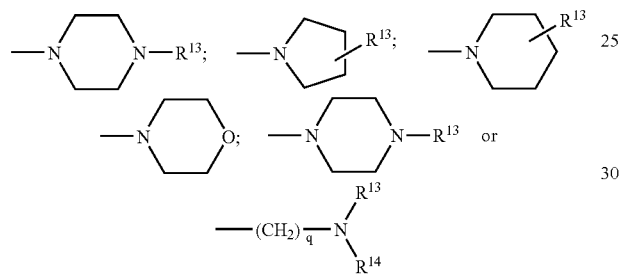

R$^{11}$ is hydrogen or C$_1$-C$_6$ alkyl, branched or unbranched, which may also be substituted by a phenyl ring which may also carry an R$^9$ radical, and R$^{12}$ is selected from the group consisting of hydrogen, C$_1$-C$_4$-alkyl, branched or unbranched, —O—C$_1$-C$_4$-alkyl, OH, Cl, F, Br, I, CF$_3$, NO$_2$, NH$_2$, CN, COOH, COO—C$_1$-C$_4$-alkyl, —NHCO—C$_1$-C$_4$-alkyl, —NHCO-phenyl, —NHSO$_2$—C$_1$-C$_4$-alkyl, NHSO$_2$-phenyl, —SO$_2$—C$_1$-C$_4$-alkyl or SO$_2$-phenyl, and R$^{13}$ is hydrogen or C$_1$-C$_6$-alkyl, linear or branched, which may be substituted by a phenyl ring which may itself also be substituted by one or two R$^{12}$ radicals, and R$^{14}$ is hydrogen or C$_1$-C$_6$-alkyl, linear or branched, which may be substituted by a phenyl ring which may itself also be substituted by one or two R$^{12}$ radicals, and n is a number 0, 1 or 2, and m and q are, independently of one another, a number 0, 1, 2, 3 or 4.

2. An amide of the formula I as claimed in claim 1 where:
A is —CH$_2$—R$^1$;
B is phenyl;
D is —CH=CH—;
R$^2$ is hydrogen;
R$^3$ is benzyl, CH$_2$—CH$_3$, CH$_2$—CH$_2$—CH$_3$, CH$_2$CH$_2$CH$_2$CH$_3$, or CH$_2$CH$_2$CH$_2$CH$_2$CH$_3$;
R$^4$ is hydrogen and
all the remaining variables have the same meaning as in claim 1.

3. An amide of the formula I as claimed in claim 1, where:
A is —CH$_2$—R$^1$;
B is phenyl;
D is —CH=CH—;
R$^2$ is hydrogen;
R$^3$ is benzyl, CH$_2$—CH$_3$, CH$_2$—CH$_2$—CH$_3$, CH$_2$CH$_2$CH$_2$CH$_3$, or CH$_2$CH$_2$CH$_2$CH$_2$CH$_3$;
R$^4$ is CO—NH$_2$ and
all the remaining variables have the same meaning as in claim 1.

4. A pharmaceutical preparation composition for oral, parenteral or intraperitonal use, comprising at least one amide of claim 1 per single dose, and conventional pharmaceutical ancillary substances.

* * * * *